(12) United States Patent
Arai

(10) Patent No.: US 10,499,796 B2
(45) Date of Patent: Dec. 10, 2019

(54) TREATMENT DEVICE AND TREATMENT SYSTEM

(71) Applicant: OLYMPUS CORPORATION, Tokyo (JP)

(72) Inventor: Norimasa Arai, Tama (JP)

(73) Assignee: OLYMPUS CORPORATION, Tokyo (JP)

(*) Notice: Subject to any disclaimer, the term of this patent is extended or adjusted under 35 U.S.C. 154(b) by 133 days.

(21) Appl. No.: 15/202,616

(22) Filed: Jul. 6, 2016

(65) Prior Publication Data

US 2018/0008126 A1  Jan. 11, 2018

(51) Int. Cl.
*A61B 1/00* (2006.01)
*A61B 17/34* (2006.01)
(Continued)

(52) U.S. Cl.
CPC ........ *A61B 1/00154* (2013.01); *A61B 1/0051* (2013.01); *A61B 1/00066* (2013.01);
(Continued)

(58) Field of Classification Search
CPC ....... A61B 1/233; A61B 1/267; A61B 1/2673; A61B 1/2676; A61B 1/24; A61B 1/00066; A61B 1/00112; A61B 1/00119; A61B 1/00121; A61B 1/00128; A61B 1/00142; A61B 1/0125; A61B 1/00068; A61B 1/00131; A61B 1/00133; A61B 1/00135;
(Continued)

(56) References Cited

U.S. PATENT DOCUMENTS

| | | | |
|---|---|---|---|
| 2008/0214890 A1* | 9/2008 | Motai ................ | A61B 1/00135 600/107 |
| 2010/0099946 A1* | 4/2010 | Jenkins ................ | A61B 1/0014 600/104 |

(Continued)

FOREIGN PATENT DOCUMENTS

| JP | 9-154803 A | 6/1997 |
|---|---|---|
| JP | 2012-254188 A | 12/2012 |
| JP | 2015-177914 A | 10/2015 |

OTHER PUBLICATIONS

International Search Report dated Sep. 19, 2017 and International Preliminary Report and Written Opinion received in PCT/JP2017/023236.

*Primary Examiner* — Ryan N Henderson
(74) *Attorney, Agent, or Firm* — Scully, Scott, Murphy & Presser, P.C.

(57) ABSTRACT

A treatment device used together with an endoscope, has a guide pipe and a movement mechanism. The guide pipe has a first pipe having a curving portion and a second pipe continuous with a proximal side of the curving portion. The curving portion has, in its inner circumferential surface, a bent surface bent to the second pipe, and bending the flow direction of the fluid discharged from the distal end of the sheath in a state where the distal end of the sheath is located near the distal end of the second pipe. The movement mechanism protrudes a distal surface of the insertion portion from the distal end of the sheath and brings the distal surface closer to or into abutment with the bent surface in a state where the distal end of the sheath is disposed near the distal end of the second pipe.

11 Claims, 25 Drawing Sheets

(51) Int. Cl.
*A61B 1/015* (2006.01)
*A61B 1/005* (2006.01)
*A61B 17/00* (2006.01)

(52) U.S. Cl.
CPC ...... *A61B 1/00068* (2013.01); *A61B 1/00133* (2013.01); *A61B 1/00135* (2013.01); *A61B 1/00147* (2013.01); *A61B 1/015* (2013.01); *A61B 17/3421* (2013.01); *A61B 2017/00292* (2013.01); *A61B 2017/00367* (2013.01); *A61B 2017/345* (2013.01)

(58) Field of Classification Search
CPC ............ A61B 1/00147; A61B 1/00154; A61B 2017/00292; A61B 2017/00296; A61B 2017/00336; A61B 2017/345; A61B 2017/3443; A61B 2017/00367; A61B 2017/00371; A61B 2017/00376; A61B 2017/00384; A61B 2017/00389; A61B 2017/0393; A61B 17/3421
See application file for complete search history.

(56) References Cited

U.S. PATENT DOCUMENTS

| | | | | |
|---|---|---|---|---|
| 2011/0301415 | A1* | 12/2011 | Motai | A61B 1/00154 600/114 |
| 2012/0071856 | A1* | 3/2012 | Goldfarb | A61B 17/24 604/514 |
| 2012/0316394 | A1 | 12/2012 | Yoshida et al. | |
| 2015/0190041 | A1 | 7/2015 | Suehara et al. | |

* cited by examiner

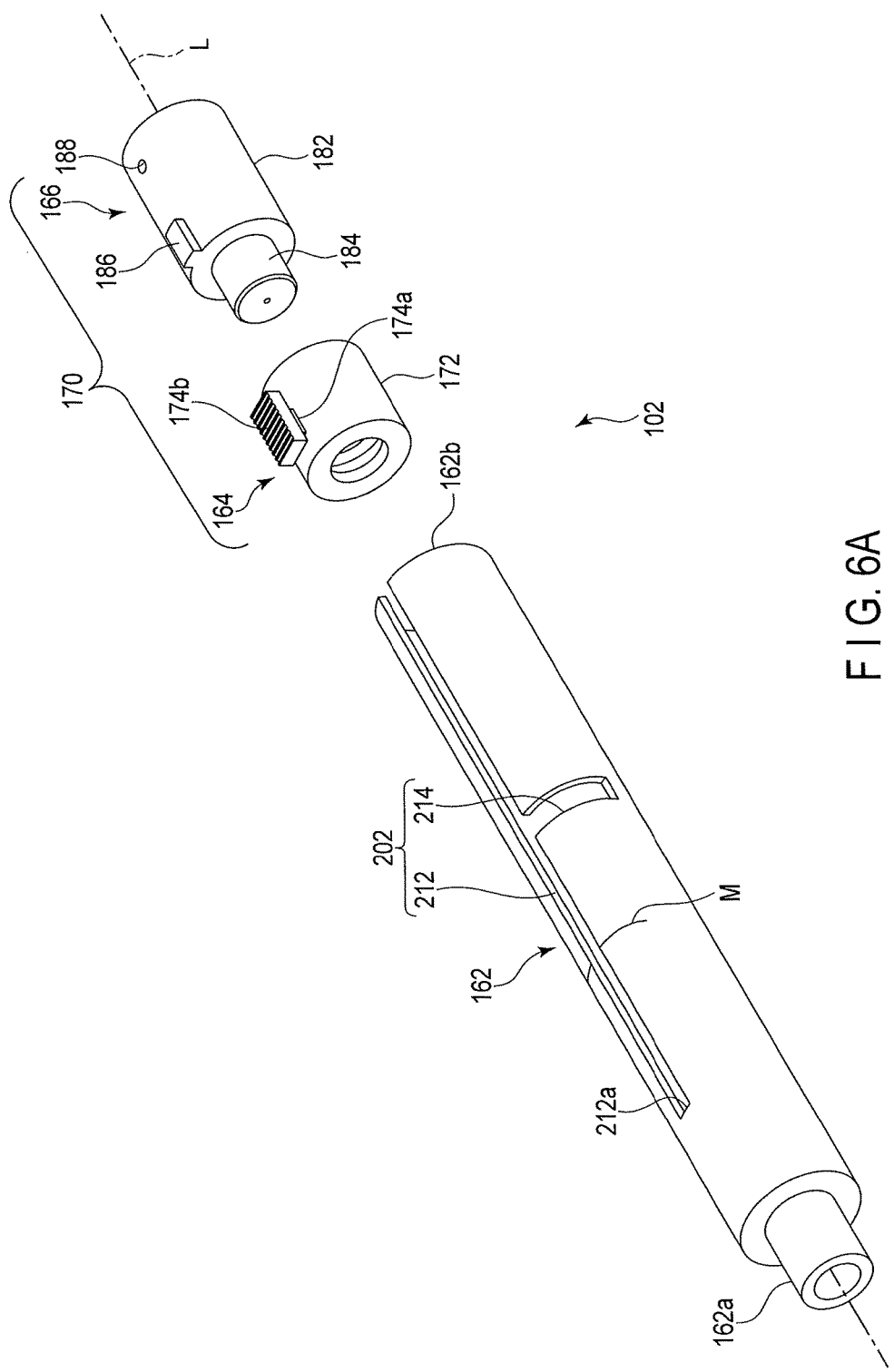
F I G. 6A

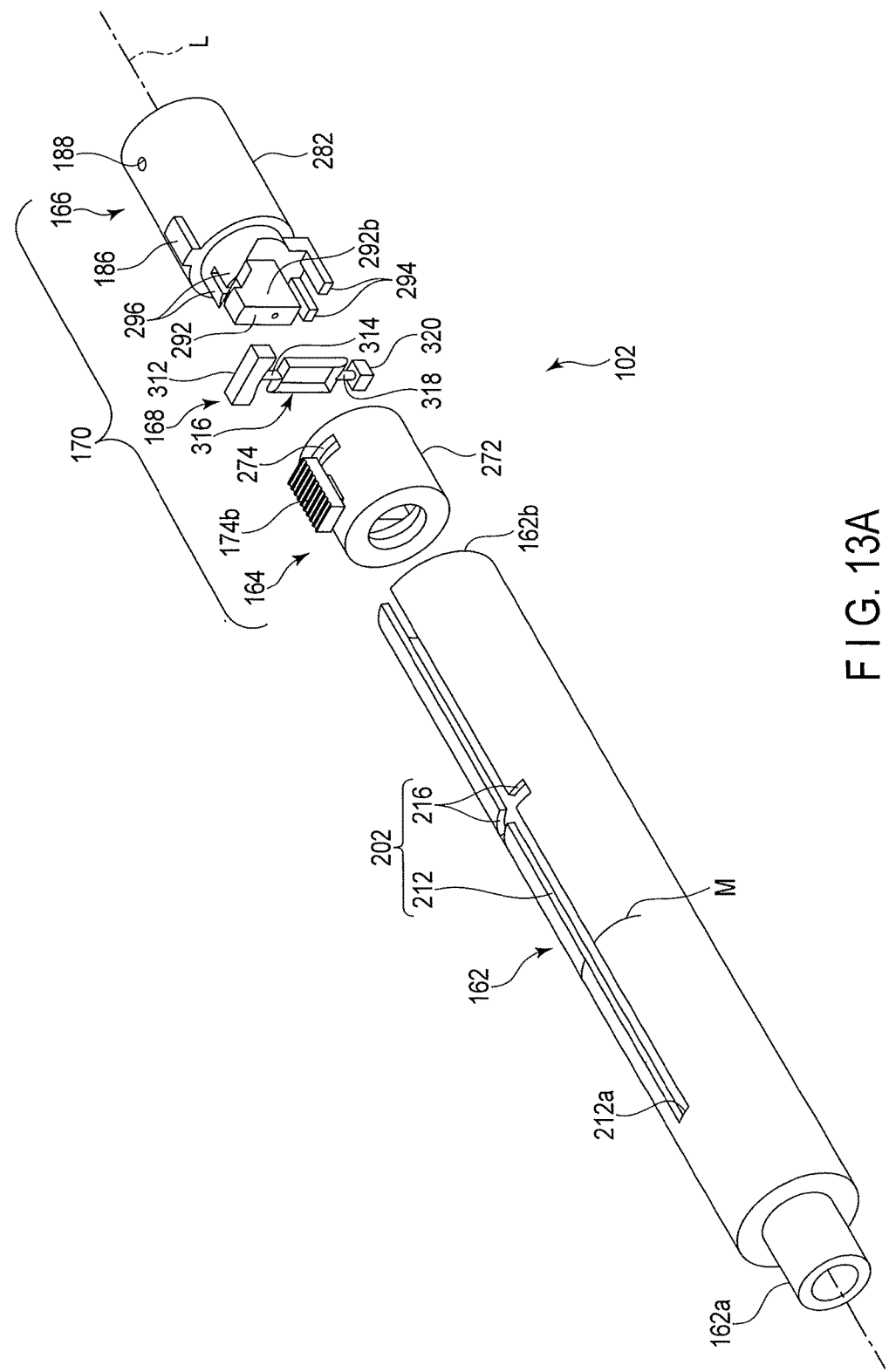
F I G. 13A

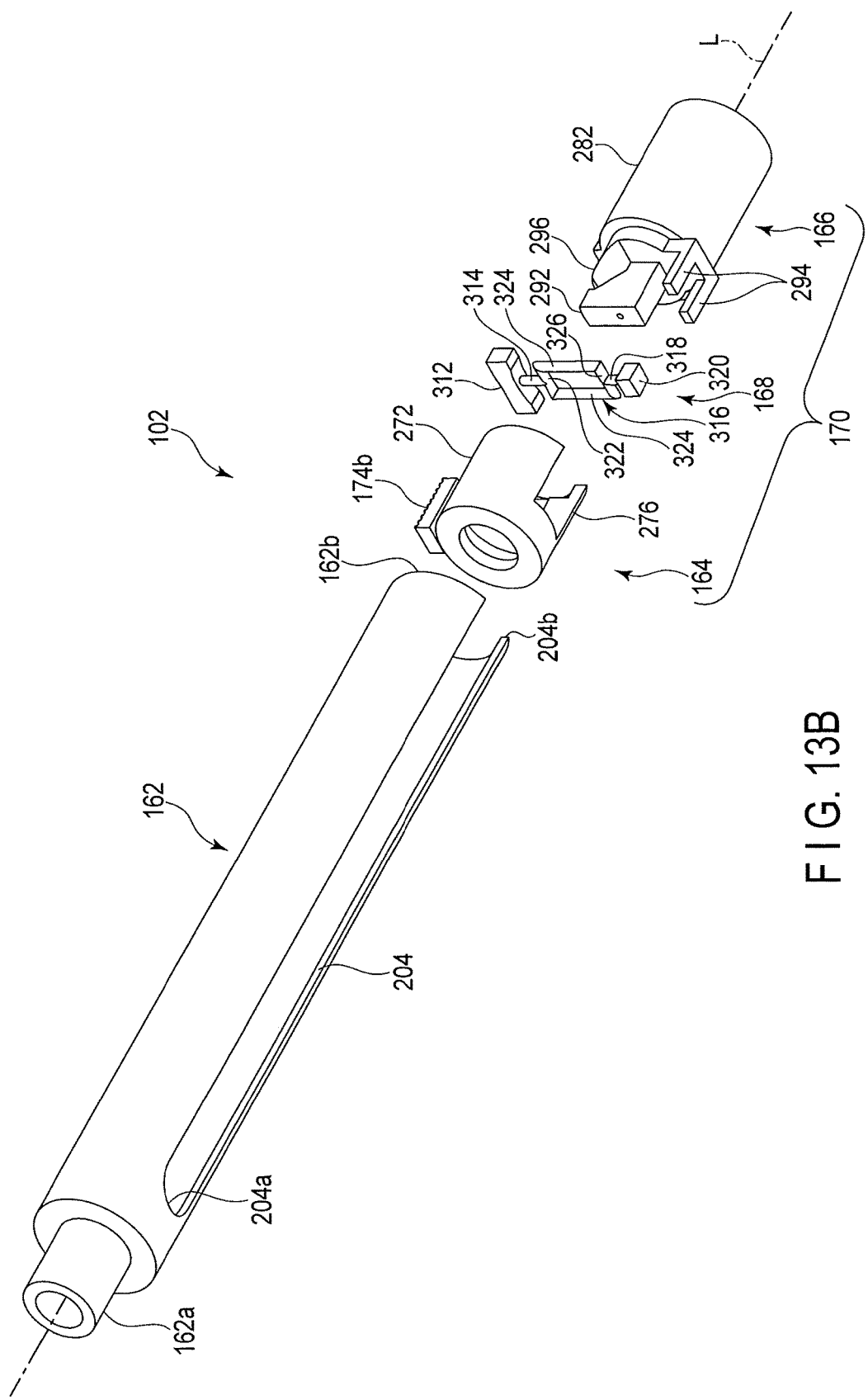
F I G. 13B

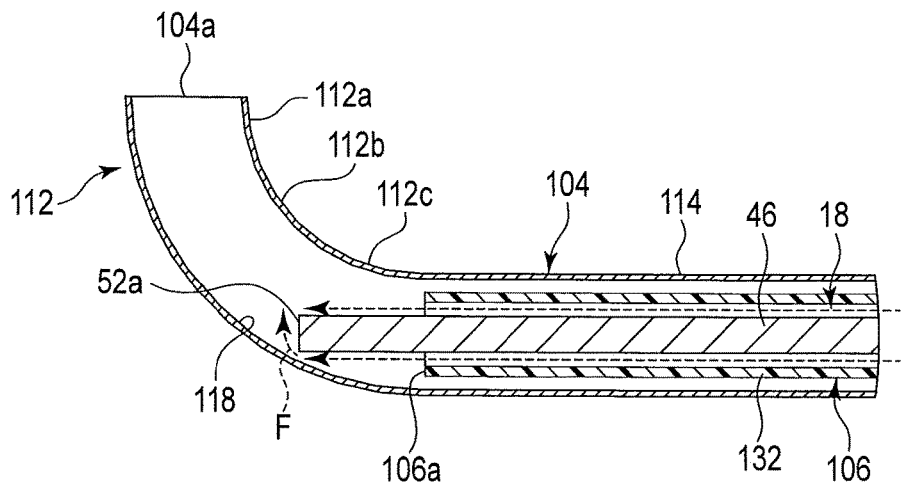
F I G. 19A
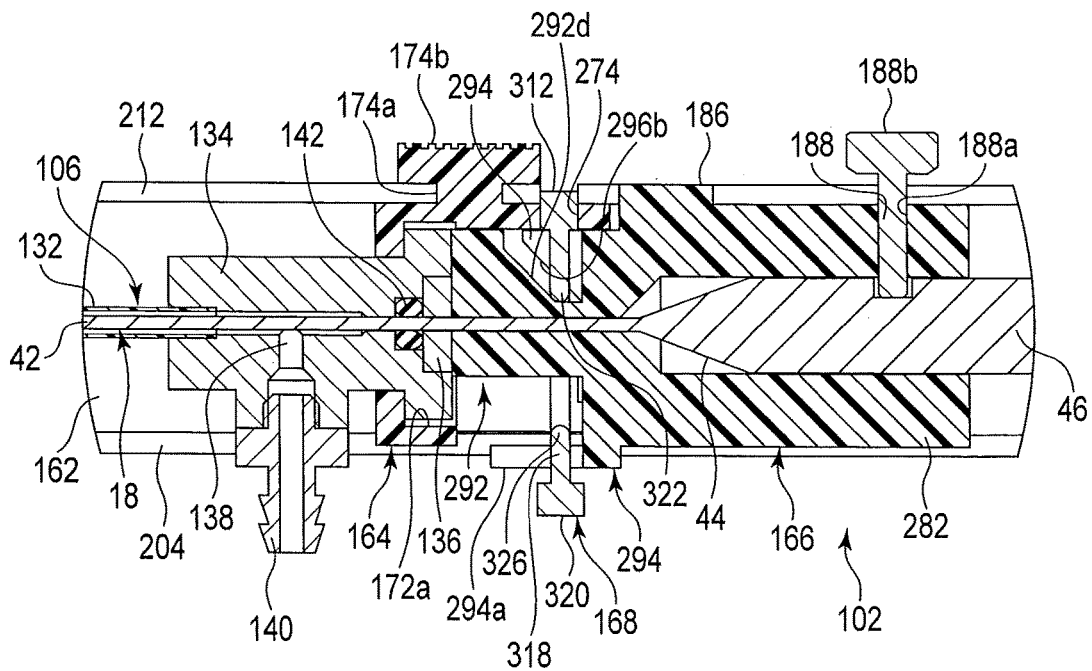
F I G. 19B

# TREATMENT DEVICE AND TREATMENT SYSTEM

BACKGROUND OF THE INVENTION

1. Field of the Invention

This invention relates to a treatment device and a treatment system.

2. Description of the Related Art

For example, JP2015-177914A discloses a cleaner capable of cleaning a distal surface of a long component. This cleaner discharges a cleaning fluid from an opening formed in a direction that intersects at right angles with the distal surface.

BRIEF SUMMARY OF THE INVENTION

According to one aspect of the present invention, there is provided a treatment device which is used together with an endoscope, the treatment device includes: a sheath through which an insertion portion of the endoscope is inserted and which forms a passage of a fluid between the sheath and the outer circumferential surface of the insertion portion of the endoscope; a guide pipe provided outside the sheath, the guide pipe including a first pipe which has a curving portion and an opening formed at a distal side of the curving portion and allowing a distal surface of the insertion portion of the endoscope and the distal end of the sheath to protrude from the opening of the guide pipe, and a second pipe which is continuous with a proximal side of the curving portion of the first pipe, the curving portion having, in its inner circumferential surface, a bent surface which is bent relative to the second pipe and which bends the flow direction of the fluid to be discharged from the distal end of the sheath in a state where the distal end of the sheath is located in the vicinity of the distal end of the second pipe; a grip disposed on a proximal side of the second pipe; and a movement mechanism which is provided in the grip and which protrudes the distal surface of the insertion portion of the endoscope from the distal end of the sheath and then brings the distal surface of the insertion portion of the endoscope closer to or into abutment with the bent surface in a state where the distal end of the sheath is disposed in the vicinity of the distal end of the second pipe.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6A is a schematic exploded perspective view in which a handle unit of the treatment device is seen from a position where a first guide passage can be observed, in the treatment system according to the first embodiment;

FIG. 13A is a schematic exploded perspective view in which the handle unit of the treatment device is seen from a position indicating the first guide passage, in the treatment system according to the second embodiment;

FIG. 13B is a schematic exploded perspective view in which the handle unit of the treatment device is seen from a position indicating a second guide passage, in the treatment system according to the second embodiment;

FIG. 19A is an enlarged diagram showing the guide pipe, the sheath, and the vicinity of the distal end of the insertion portion of the endoscope at a position indicated by a sign 19A in FIG. 17B; and FIG. 19B is an enlarged diagram showing the grip, the first operating body, the second operating body, the switch button, the guide pipe, the sheath, and the endoscope at a position indicated by a sign 19B in FIG. 17B.

DETAILED DESCRIPTION OF THE INVENTION

Hereinafter, embodiments of this invention will be described with reference to the drawings.

The first embodiment is described with reference to FIG. 1 to FIG. 11B.

Figure 1:
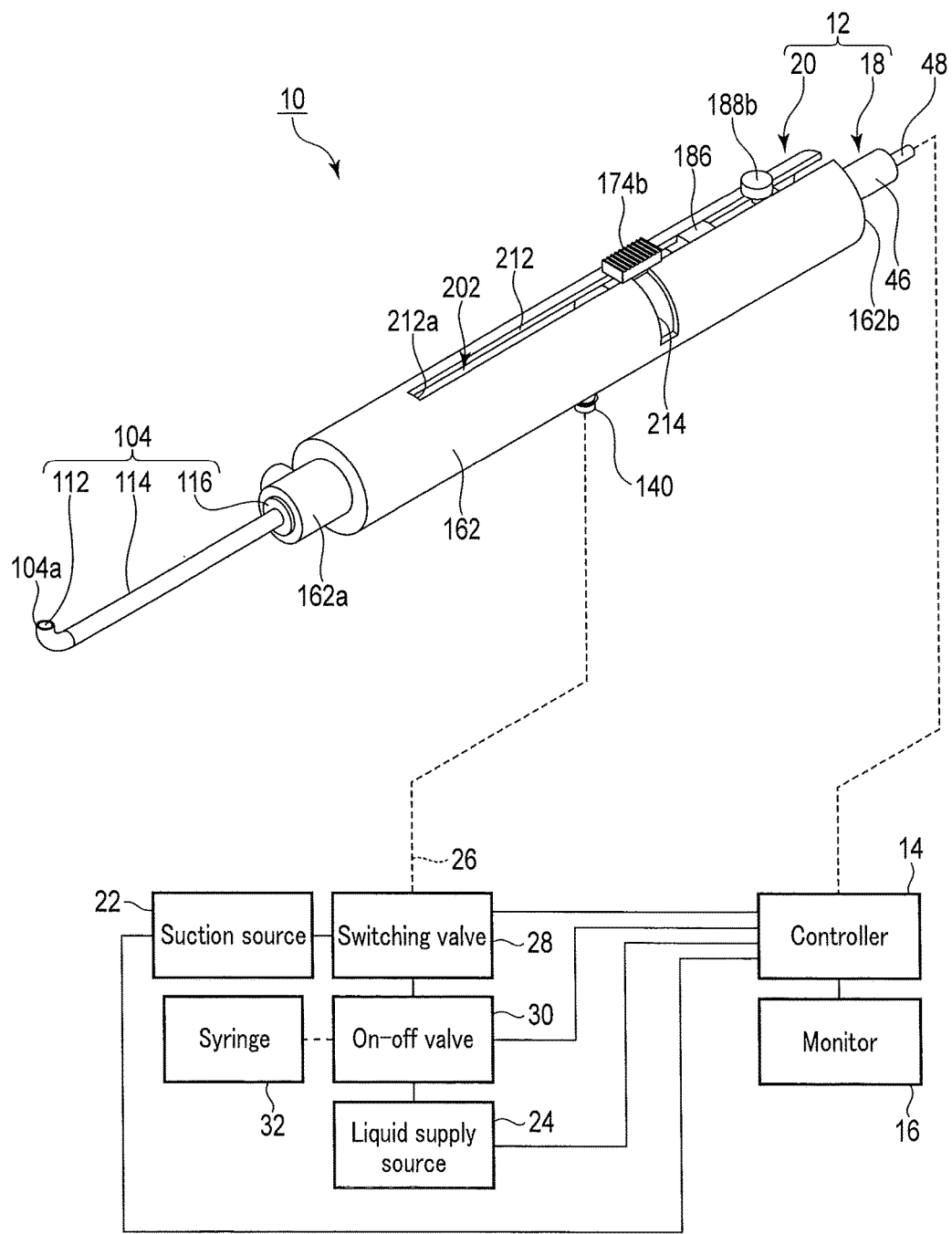
FIG. 1 is a schematic diagram showing a treatment system (endoscope system) according to a first embodiment.

As shown in FIG. 1, a treatment system (endoscope system) 10 according to this embodiment includes a treatment device unit (endoscope insertion assist unit) 12, a controller 14, and a monitor 16. The treatment system 10 and the treatment device unit 12 according to the present embodiment are mainly used to treat and observe paranasal sinuses. Thus, an example of the treatment and observation of paranasal sinuses is described in the present embodiment. It is also possible to use the treatment system 10 and the treatment device unit 12 according to the present embodiment to treat and observe parts different from paranasal sinuses.

The treatment device unit 12 includes an endoscope 18 and a treatment device (endoscope insertion assist device) 20.

A suction source 22 and a liquid supply source (liquid feed source) 24 are connectable to the treatment device 20. A switching valve 28 such as a three-way cock is provided between the end of a tube 26 extending from the treatment device 20 and the suction source 22 as well as the liquid supply source 24. Thus, the user can selectively use the suction source 22 and the liquid supply source 24 for the treatment device 20 by the operation of the switching valve 28. It is also appropriate that an on-off valve 30 such as a three-way cock to which a syringe 32 is detachably connectable, for example, for medication be provided, for example, between the switching valve 28 and the liquid supply source 24.

A liquid to be supplied from the liquid supply source 24 is suitably selectable. The liquid supply source 24 can supply a physiological saline F to the treatment device unit 12 to clean an affected part in, for example, a paranasal sinus inside the nose. The liquid supply source 24 can further supply a chemical to treat the affected part. The chemical to be administered is mainly a steroid or an antibacterial agent. As the suction source 22, for example, suction equipment provided on the wall of an operating room can be used as it is. If the suction source 22 is activated, for example, viscous matter present in paranasal sinuses and around the affected part in a nasal cavity can be removed by use of the treatment device unit 12. When the affected part and the parts therearound are cleaned with the physiological saline F, this cleaning solution can be removed together with the viscous matter.

Figure 2:
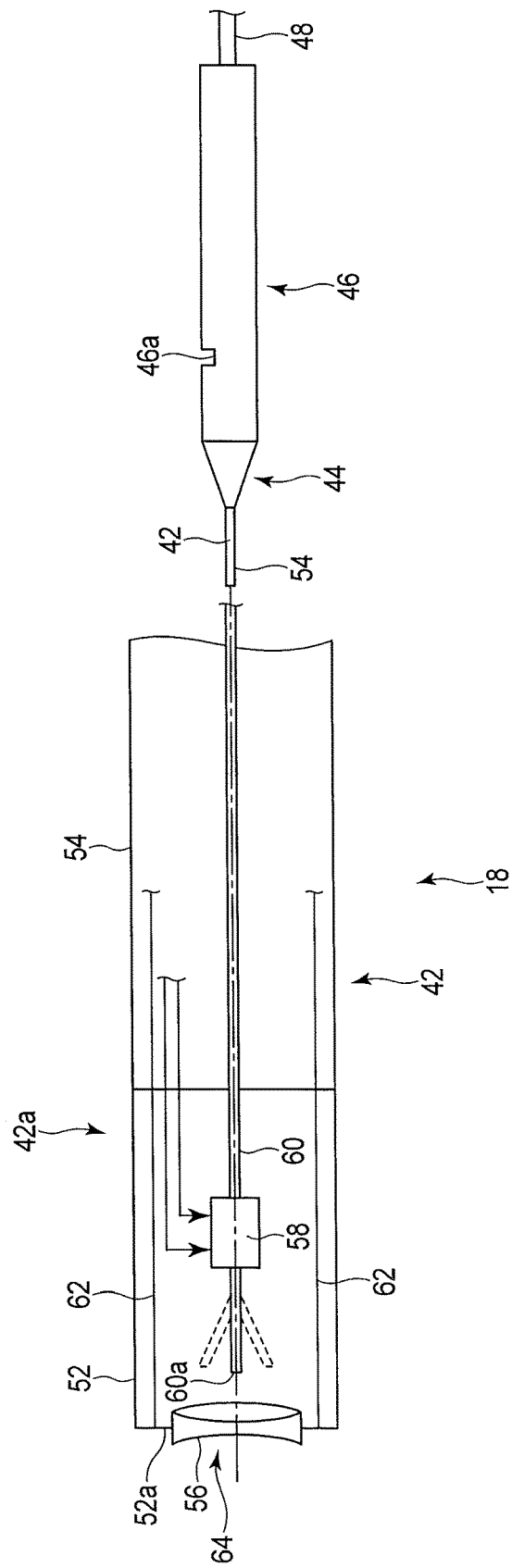
FIG. 2 is a schematic diagram showing an endoscope for use in the treatment system according to the first and second embodiments.

The endoscope 18 is attached to the treatment device 20 in use. As shown in FIG. 2, the endoscope 18 includes an insertion portion 42, an anti-break 44, a support portion 46, and a cable 48. The insertion portion 42 can protrude relative to a later-described distal opening 104a of a guide pipe 104.

The endoscope 18 can load an image of a part facing a later-described distal surface 52a of the insertion portion 42 and then display the image on the monitor 16. An endoscope 18 of any type such as a fiber type or an image pickup device type including a CCD or a CMOS may be used, but a scan type is preferably used here.

The scan type endoscope 18 is known and is therefore not described in detail. The internal structure of a distal end 42a of the insertion portion 42 is formed as shown in FIG. 2. This scan type endoscope 18 allows the insertion portion 42 to be formed with a smaller diameter than the fiber type or the image pickup device type. Thus, the scan type endoscope 18 is preferably used to be put through an extremely narrow cavity such as a paranasal sinus.

As shown in FIG. 2, the insertion portion 42 of the endoscope 18 includes a distal hard portion 52, a flexible tube 54, an illumination window (optical element) 56, an actuator 58, an illumination fiber 60, and light-receiving fibers 62. Among the above, the illumination window 56, the actuator 58, the illumination fiber 60, and the light-receiving fibers 62 constitute an observation optical system 64. That is, the observation optical system 64 is provided inside the insertion portion 42. In the observation optical system 64, the actuator 58, the illumination fiber 60, and the light-receiving fibers 62 are each connected optically and/or electrically to the controller 14 shown in FIG. 1.

The controller 14 shown in FIG. 1 controls the observation optical system 64 of the endoscope 18. The controller 14 controls the operation of the actuator 58. The controller 14 has, for example, an unshown light source such as a white light, and allows light for observation to suitably enter the illumination fiber 60. The controller 14 converts the light received by the light-receiving fibers 62 into an image.

The distal hard portion 52, the illumination window 56, the actuator 58, the distal end of the illumination fiber 60, and the distal ends of the light-receiving fibers 62 are provided at the distal end 42a of the insertion portion 42.

The illumination window 56 and the distal ends of the light-receiving fibers 62 are fixed to the distal surface (distal end) 52a of the distal hard portion 52. The distal ends of the light-receiving fibers 62 are fixed to the part around the illumination window 56 at suitable intervals.

In the distal hard portion 52, the actuator 58 is provided on the proximal side of the illumination window 56. The actuator 58 supports the distal end (the part closer to the proximal side than the distalmost part) of the illumination fiber 60. The actuator 58 is swung, for example, in a spiral form by the controller 14. Thus, a distal end 60a of the illumination fiber 60 is swung in a spiral form in accordance with the operation of the actuator 58. Therefore, the surface of a subject is scanned with illumination light in a spiral form through the distal end of the illumination fiber 60 and the illumination window 56. The light-receiving fibers 62 receive return light from the subject and then guide the light to the controller 14. The controller 14 shown in FIG. 1 converts the light received by the light-receiving fibers 62 into an image, and displays the imaged figure on the monitor 16 connected to the controller 14.

The flexible tube 54 is provided on the proximal side of the distal hard portion 52. The flexible tube 54 extends toward the proximal side from the proximal end of the distal hard portion 52. The entire length of the insertion portion 42 is mostly formed as a flexible part by the flexible tube 54. The anti-break 44 is fixed to the proximal end of the flexible tube 54. The support portion 46 is fixed to the proximal end of the anti-break 44. The cable 48 is fixed to the proximal end of the support portion 46. The proximal end of the cable 48 is connected to the controller 14.

The support portion 46 of the endoscope 18 has a recess 46a which is fixed to an external thread 188b of a later-described second operating body 166. The direction (normal direction) of the recess 46a corresponds to the upper side of the figure which is displayed on the monitor 16. The support portion 46 of the endoscope 18 is always fixed in the same direction relative to the second operating body 166 by the recess 46a. Thus, the direction of the figure of the endoscope 18 which is displayed on the monitor 16 is defined.

Figure 3:
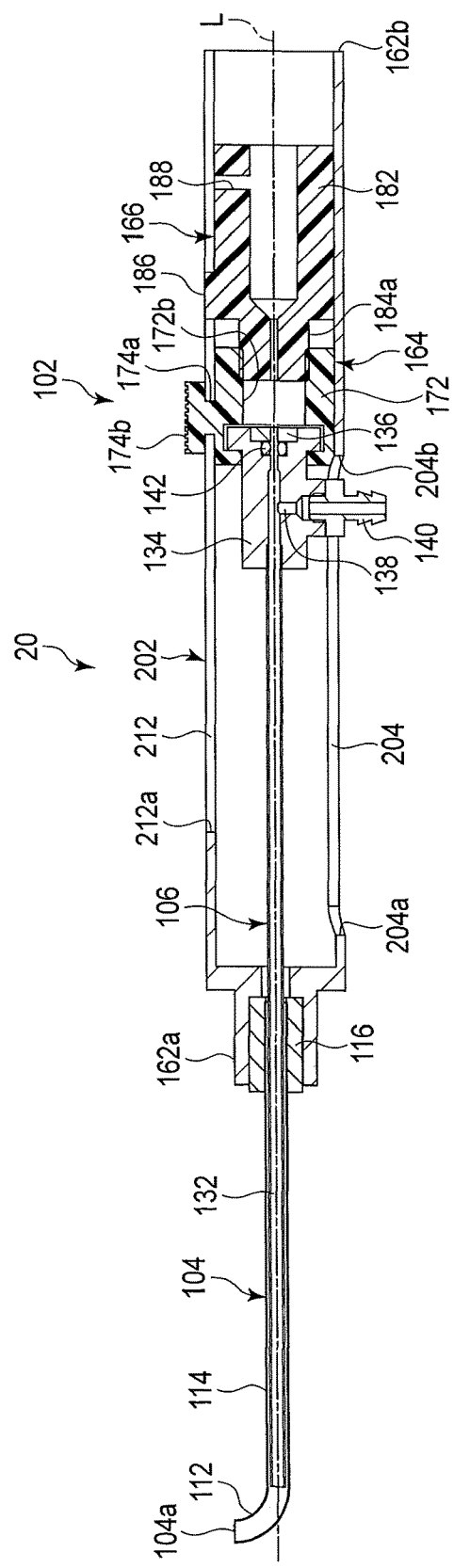
FIG. 3 is a schematic sectional view showing a treatment device of the treatment system according to the first embodiment.

As shown in FIG. 3, the treatment device 20 includes a handle unit 102, the guide pipe 104, and a sheath 106. The handle unit 102 is grasped and suitably operated by the user.

Figure 4A:
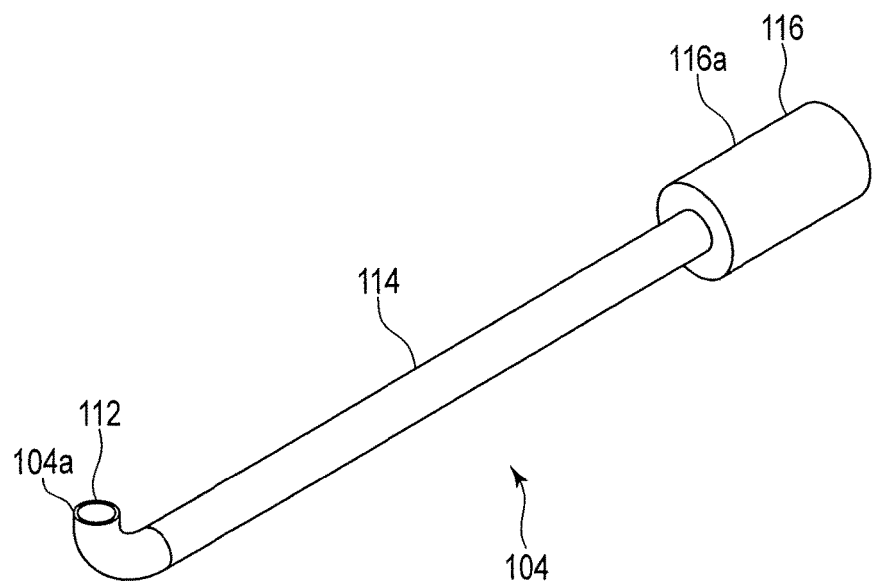
FIG. 4A is a schematic perspective view showing a guide pipe for use in the treatment system according to the first and second embodiments.
Figure 4B:
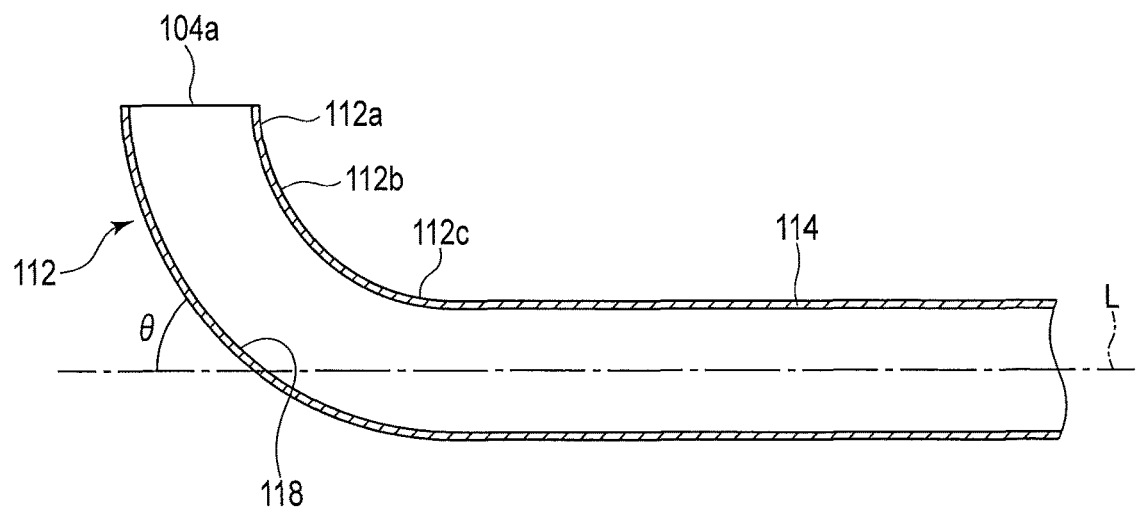
FIG. 4B is a schematic diagram showing a section of a bent pipe and the vicinity of the distal end of a straight pipe of the guide pipe for use in the treatment system according to the first and second embodiments.

As shown in FIG. 4A, the guide pipe 104 is formed by a bent pipe (first pipe) 112 and a straight pipe (second pipe) 114 that are continuous with each other. The guide pipe 104 has an internal diameter through which the insertion portion 42 of the endoscope 18 and a later-described sheath body 132 of the sheath 106 can be inserted. As shown in FIG. 4B, an angle θ of the bent pipe 112 to the straight pipe 114 is set to a suitable state. The angle θ may be any one of an acute angle, a right angle, and an obtuse angle.

The bent pipe 112 has a distal end 112a which is fitted into the entrance of a paranasal sinus, a guide portion 112b formed continuously with the distal end 112a, and a curving portion (guide pipe curving portion) 112c which is formed continuously with the guide portion 112b and which is integrated with the distal end of the straight pipe 114. A part from the proximal end of the bent pipe 112 to the distal opening 104a deviates from a later-described longitudinal axis L. It is preferable that, depending on the shape of the bent pipe 112, no guide portion 112b be present and the distal end 112a be formed continuously with the curving portion 112c. The guide pipe 104 in which the bent pipe 112 is bent as shown in FIG. 4A is used to observe and treat, for example, a frontal sinus among paranasal sinuses. Although not shown, this guide pipe 104 is used to observe and treat, for example, the maxillary sinus, for example, when the angle θ is more than a right angle.

An inner circumferential side region indicated by a sign 118 on the proximal side in the inner circumferential surface of the curving portion 112c changes the direction of the distal surface 52a of the insertion portion 42 of the endoscope 18 toward the distal end 112a and the distal opening 104a of the guide pipe 104 when the distal surface 52a is brought into abutment with this region. Thus, a bent surface 118 is formed in the inner circumferential surface of the curving portion 112c to change a direction of the distal hard portion 52 of the insertion portion 42 of the endoscope 18 and change the direction of the distal surface 52a of the insertion portion 42 of the endoscope 18 toward the opening of the distal end 112a. Although described later, this bent surface 118 is also used to change the direction of the physiological saline F when a suitable volume of the physiological saline F is discharged from a distal opening 106a of the sheath 106.

The straight pipe 114 of the guide pipe 104 extends along the longitudinal axis L. The straight pipe 114 may be made of a rigid material such as a stainless steel material, or may be made of a combination of a rigid material and a flexible material such as a silicone material. In the example shown in FIG. 4A, the part from the proximal end of the straight pipe 114 to the bent pipe 112 is seamlessly and integrally formed by a stainless steel material.

As shown in FIG. 4A, a holder 116 is fixed to the proximal end of the straight pipe 114 of the guide pipe 104. The holder 116 is fixed to a later-described grip 162 of the handle unit 102. The holder 116 is fixed in a predetermined direction relative to a distal end 162a of the grip 162 of the handle unit 102.

The distal opening 104a of the guide pipe 104 is formed to have an inside diameter larger than the outside diameter of the distal opening 106a of the sheath 106 such that the distal surface 52a of the insertion portion 42 of the endoscope 18 can be put therethrough and such that the distal opening 106a of the sheath 106 can be put therethrough.

Therefore, the straight pipe 114 of this guide pipe 104 permits the sheath 106 to move therein in a state where the insertion portion 42 of the endoscope 18 is inserted through the sheath 106. The bent pipe 112 of the guide pipe 104 is located on the distal side of the straight pipe 114, and has an internal diameter and a bending radius such that the sheath body 132 of the sheath 106 can protrude to the distal side through the distal opening 104a of the guide pipe 104 in a state where the insertion portion 42 is inserted through the sheath 106.

Figure 5:
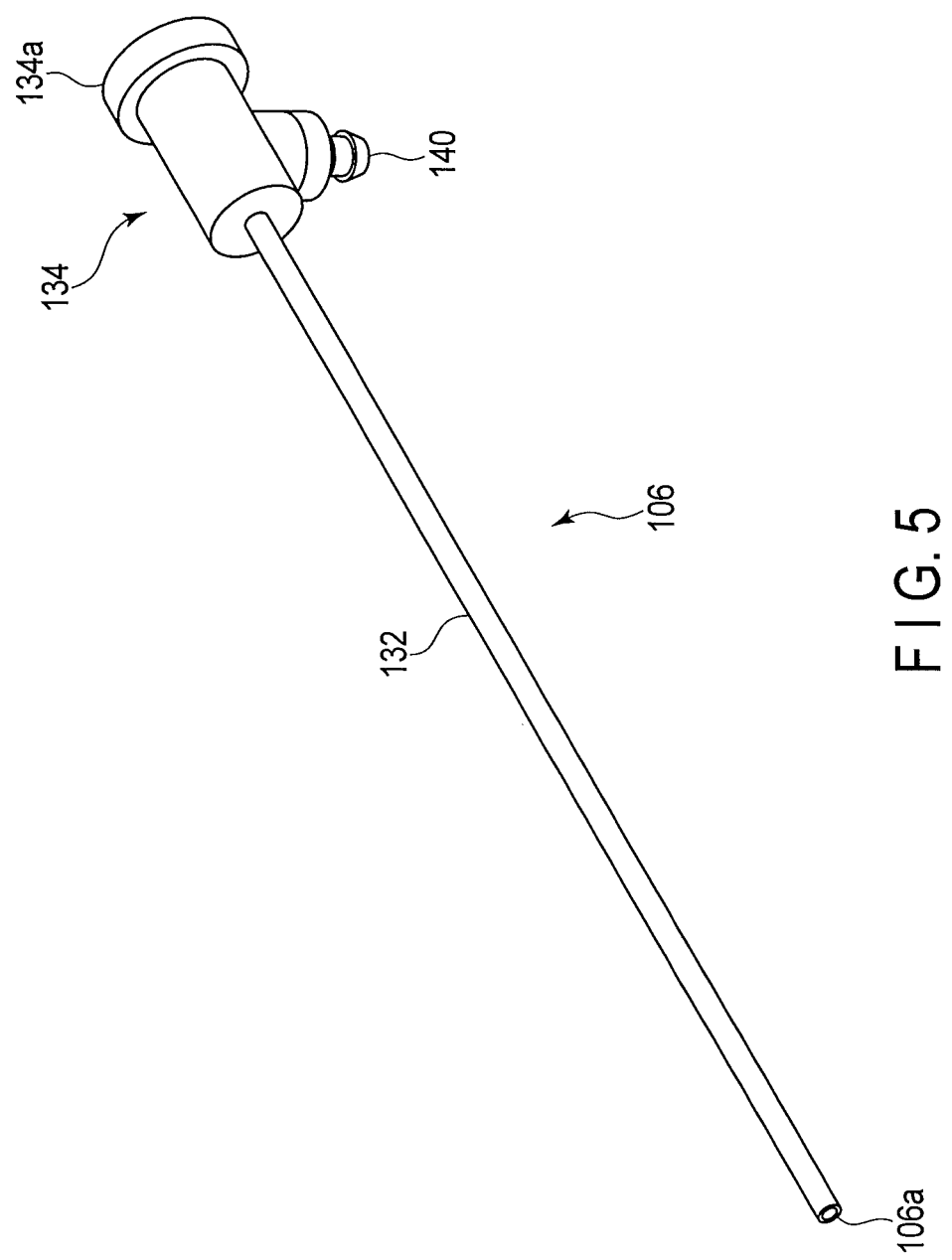
FIG. 5 is a schematic perspective view showing a sheath for use in the treatment system according to the first and second embodiments.

The insertion portion 42 of the endoscope 18 is inserted through the sheath 106, and a passage for the fluid F is formed between the sheath 106 and the outer circumferential surface of the insertion portion 42 of the endoscope 18. As shown in FIG. 5, the sheath 106 has the sheath body 132 and a sheath holder 134 in this order from the distal side to the proximal side.

The sheath body 132 is formed into a pipe shape by an elastically deformable resin material. It is appropriate that a braided pipe (not shown) called a braid be buried in the sheath body 132. Thus, the sheath body 132 according to this embodiment is more firmly formed than when simply made of a resinous material. That is, the sheath body 132 is thin, but is high in the later-described performance of following rotation around the longitudinal axis L, is easy to bend, and is formed to be difficult to break so that a hollow portion is secured therein. It is preferable that the sheath body 132 be formed to be more difficult to bend than the flexible tube 54 of the insertion portion 42 of the endoscope 18 shown in FIG. 2. Thus, it is possible to hold the position of the distal hard portion 52 in a desired state when the whole distal hard portion 52 of the insertion portion 42 and a part of the flexible tube 54 protrude from the distal opening 106a of the sheath body 132.

The sheath body 132 extends along the longitudinal axis L when its distal opening 106a is located in the straight pipe 114. When the distal opening 106a of the sheath body 132 is located in the bent pipe 112, the part of the sheath body 132 from the proximal end of the bent pipe 112 to the distal opening 106a deviates from the longitudinal axis L.

The sheath holder 134 is cylindrically formed by a rigid material such as a stainless steel material. As shown in FIG. 3, the outer circumferential surface of the proximal end of the sheath body 132 is fixed to the inner circumferential surface of the sheath holder 134, for example, by adhesion. It is appropriate that, for example, an unshown O-ring be airtightly and watertightly provided between the inner circumferential surface of the sheath holder 134 and the outer circumferential surface of the proximal end of the sheath body 132.

As shown in FIG. 3 and FIG. 5, the sheath holder 134 has a flange 134a diametrically outwardly protruding relative to the longitudinal axis L here. As shown in FIG. 3, the sheath holder 134 has, at its proximal end, a fixing plate 136 to fix an O-ring 142 to secure watertightness between the sheath holder 134 and the insertion portion 42 of the endoscope 18. The sheath holder 134 forms a T-shaped pipeline 138. The T-shaped pipeline 138 has a part which is formed along the longitudinal axis L and through which the insertion portion 42 of the endoscope 18 is inserted, and a part which extends in a direction that intersects at right angles with the longitudinal axis L and to which a tube connection portion 140 is detachably connected. That is, the tube connection portion 140 which allows the fluid to flow between the inner circumferential surface of the sheath 106 and the outer circumferential surface of the insertion portion 42 of the endoscope 18 is detachably provided in the sheath holder 134 in particular of the sheath 106. The tube connection portion 140 protrudes from a second guide passage 204 of the grip 162 of the handle unit 102 in the direction that intersects at right angles with the longitudinal axis L. The suction source 22, the liquid supply source 24, the switching valve 28, and the on-off valve 30 shown in FIG. 1 are connected to the tube connection portion 140.

The sheath body 132 has an inside diameter through which the insertion portion 42 is inserted so that the distal surface 52a of the insertion portion 42 can protrude relative to the distal opening 106a of the sheath body 132. The sheath body 132 is inserted through the guide pipe 104 so that the distal opening 106a of the sheath body 132 can protrude relative to the distal opening 104a of the guide pipe 104.

Figure 6B:
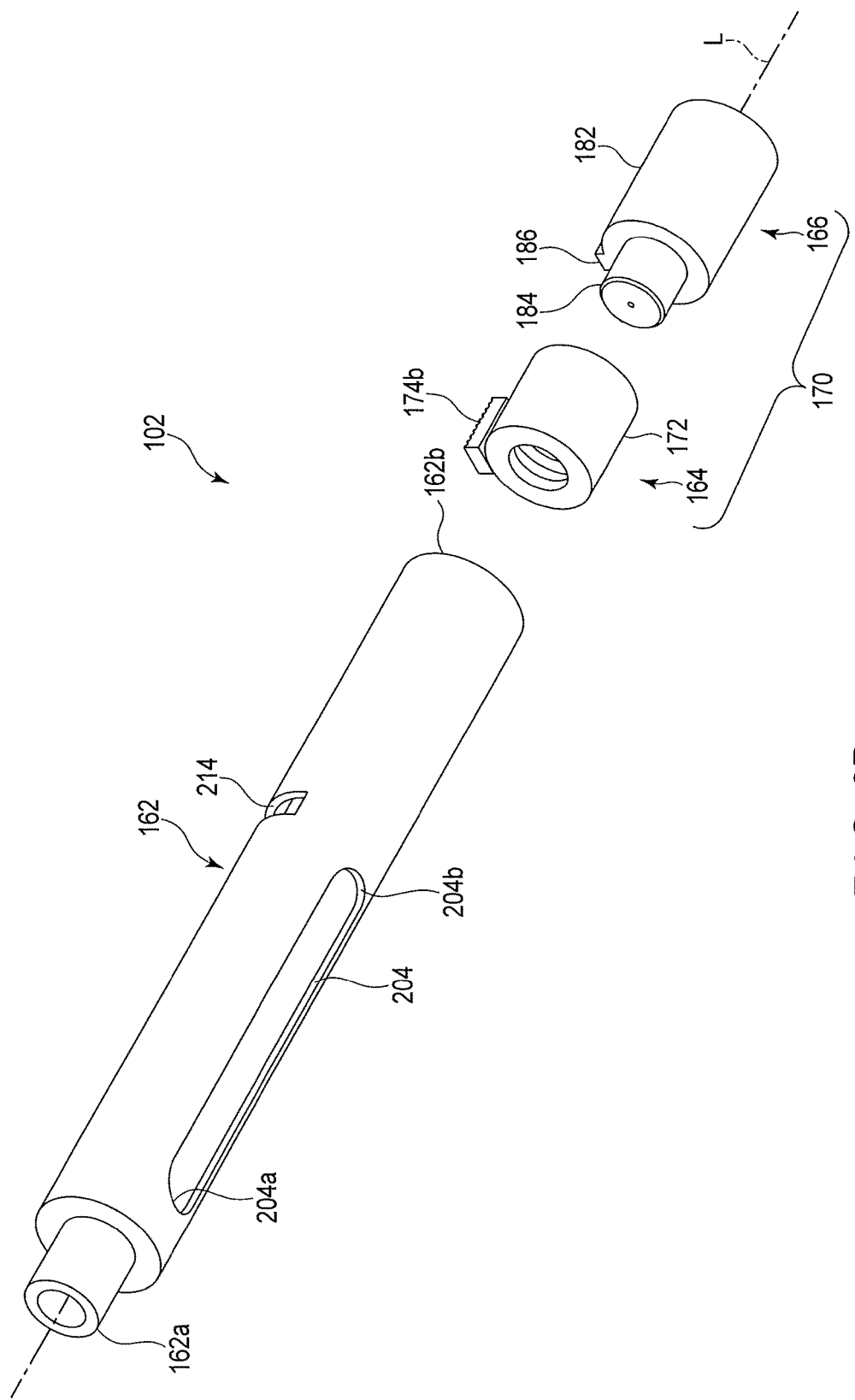
FIG. 6B is a schematic exploded perspective view in which the handle unit of the treatment device is seen from a position where a second guide passage can be observed, in the treatment system according to the first embodiment.

As shown in FIG. 6A and FIG. 6B, the handle unit 102 includes the grip 162, a first operating body 164 which supports and moves the sheath 106, and the second operating body 166 which supports and moves the insertion portion 42 of the endoscope 18. The first operating body 164 and the second operating body 166 are coupled to each other to form a movement mechanism 170.

As shown in FIG. 1, the guide pipe 104, the first operating body 164, the second operating body 166, the sheath 106, and the endoscope 18 are attached to the grip 162 of the handle unit 102. The grip 162 of the handle unit 102 defines the longitudinal axis L by its distal end 162a and proximal end 162b. As shown in FIG. 6A and FIG. 6B, the grip 162 is substantially cylindrically formed. In this shape, the inner circumferential surface of the grip 162 is substantially annular in its cross section that intersects at right angles with the longitudinal axis L.

The first operating body 164 has a cylindrical body 172. The second operating body 166 has a first cylindrical body 182 and a second cylindrical body 184. It is appropriate that the cylindrical bodies 172, 182, and 184 be annularly formed in this embodiment. The second cylindrical body 184 of the second operating body 166 is formed integrally and concentrically with the distal end of the first cylindrical body 182. The cylindrical bodies 172 and 182 have substantially the same outside diameter. The outside diameter of the cylindrical bodies 172 and 182 is formed to be slightly smaller than the inside diameter of the grip 162. Thus, as shown in FIG. 3, the outer circumferential surface of the cylindrical body 172 of the first operating body 164 and the outer circumferential surface of the cylindrical body 182 of the second operating body 166 are movable along the inner circumferential surface of the grip 162 of the handle unit 102. The cylindrical body 172 has, in its inner circumferential surface, a support portion 172a which supports the flange 134a of the sheath holder 134, and an internal-thread-shaped helical groove 172b formed closer to the proximal side than the support portion 172a along the longitudinal axis L.

The sheath holder 134 moves to follow the movement of the first operating body 164 along the longitudinal axis L because the flange 134a is supported by the support portion 172a. In contrast, the sheath holder 134 does not follow the movement of the first operating body 164 along the longitudinal axis L.

Figure 7:
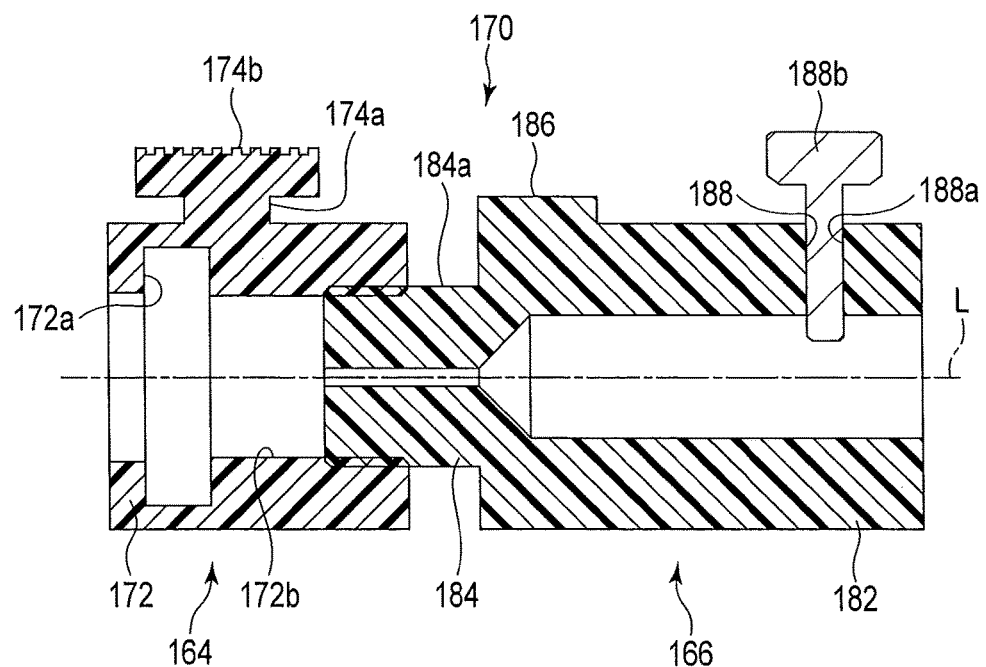
FIG. 7 is a schematic sectional view showing a state where an external-thread-shaped helical groove of a second operating body is screwed to an internal-thread-shaped helical groove of a first operating body of the handle unit of the treatment device, in the treatment system according to the first embodiment.
Figure 8A:
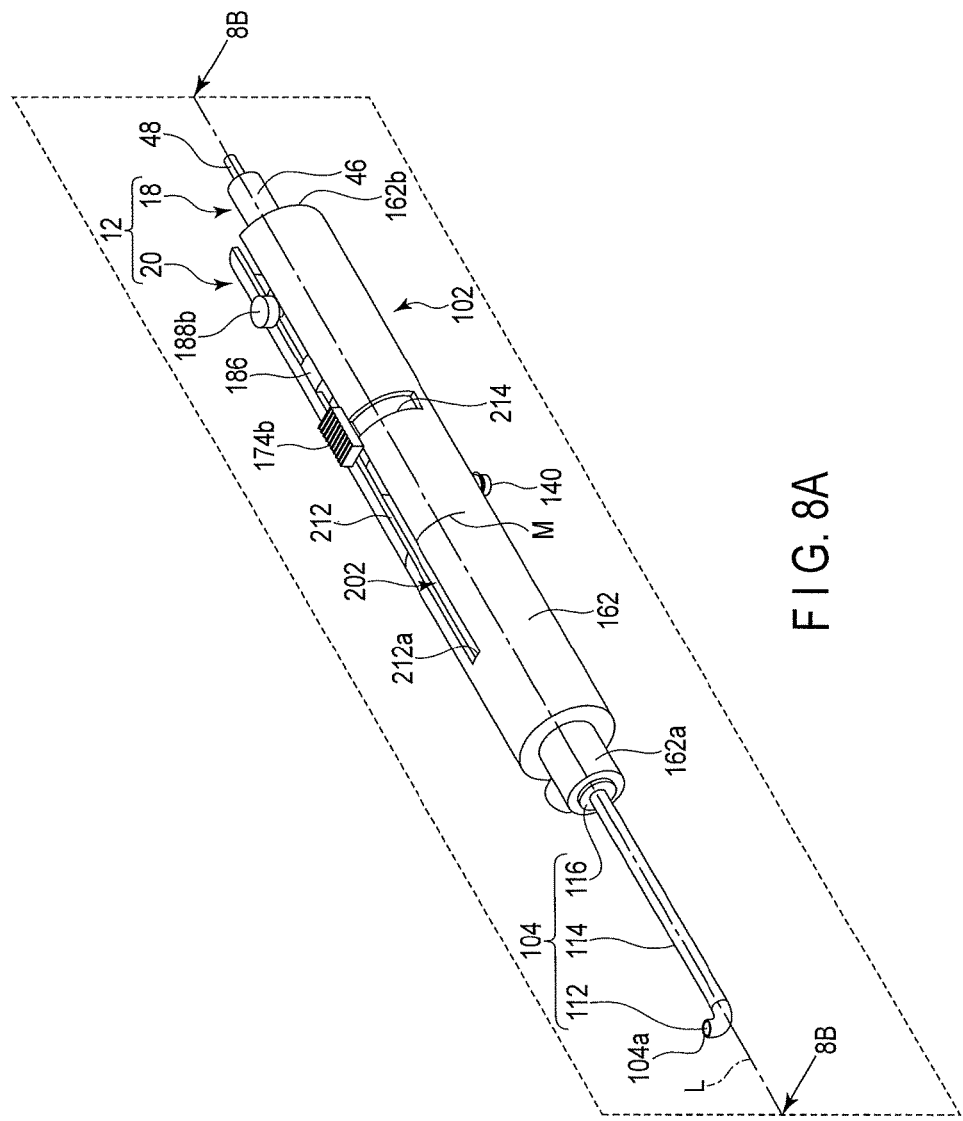
FIG. 8A is a schematic perspective view showing a state where a treatment device unit is seen from a direction similar to that in FIG. 6A, and showing a state where the inside of paranasal sinuses can be observed and treated with the treatment device unit, in the treatment system according to the first embodiment.
Figure 8B:
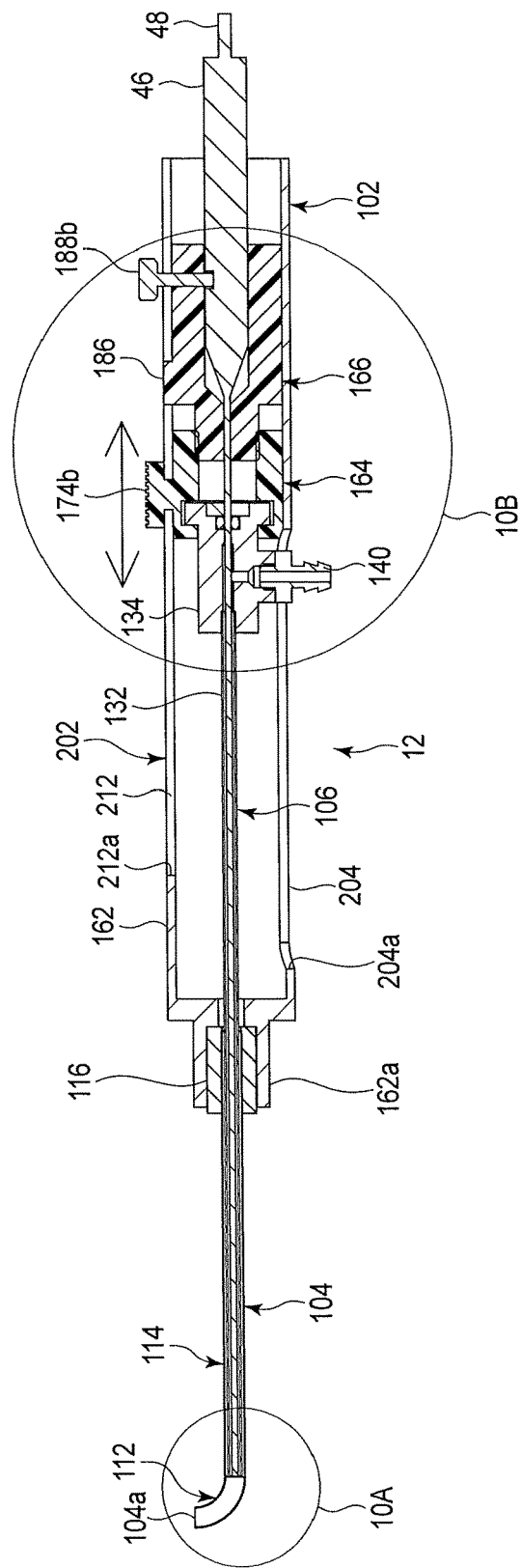
FIG. 8B is a longitudinal sectional view of the treatment device unit at a position along the line 8B-8B in FIG. 8A, in the treatment system according to the first embodiment.
Figure 9A:
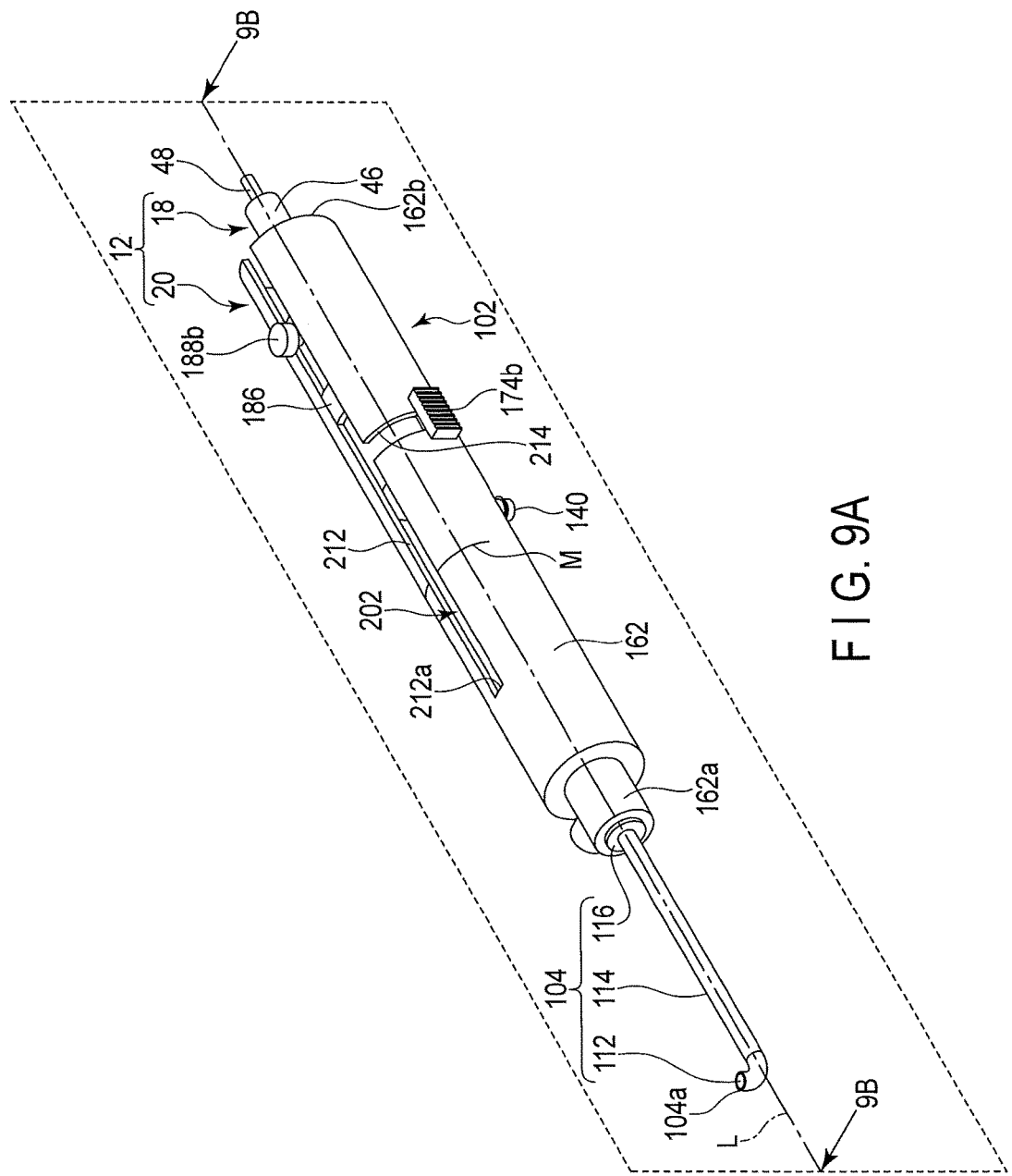
FIG. 9A is a schematic perspective view showing a state where the treatment device unit is seen from the direction similar to that in FIG. 6A, and showing a state where the distal surface of an insertion portion of the endoscope can be cleaned in the guide pipe of the treatment device unit, in the treatment system according to the first embodiment.
Figure 9B:
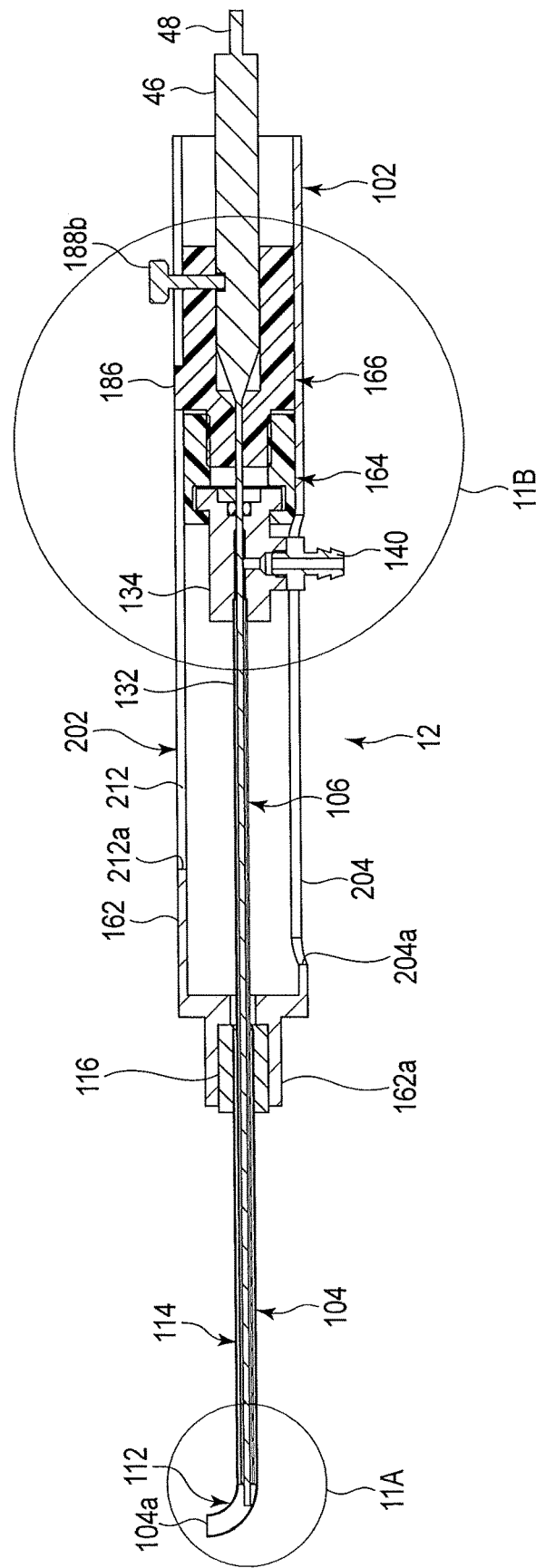
FIG. 9B is a longitudinal sectional view of the treatment device unit at a position along the line 9B-9B in FIG. 9A, in the treatment system according to the first embodiment.
Figure 10A:
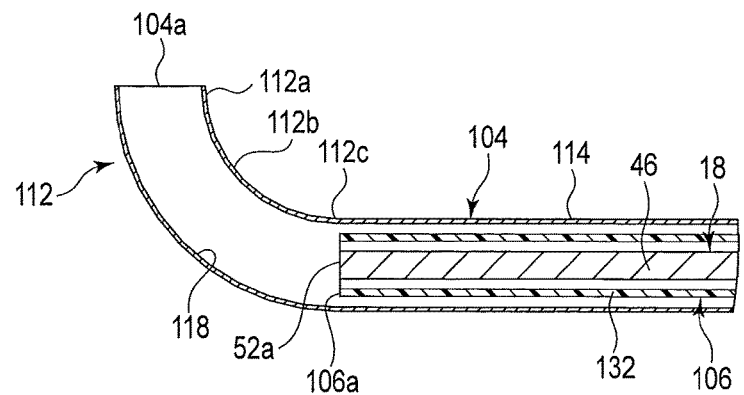
FIG. 10A is an enlarged diagram showing the guide pipe, the sheath, and the vicinity of the distal end of the insertion portion of the endoscope at a position indicated by a sign 10A in FIG. 8B.
Figure 10B:
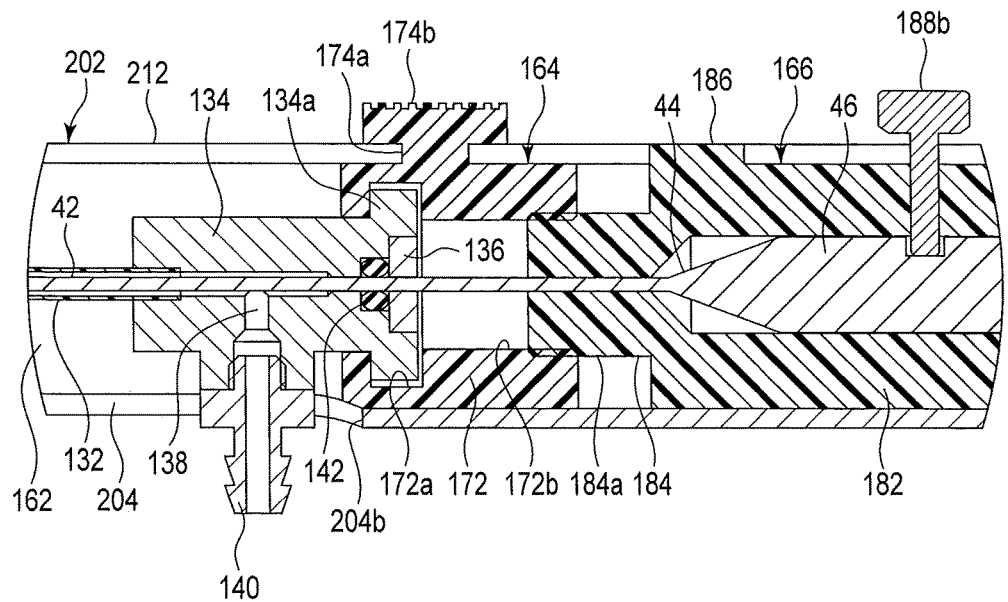
FIG. 10B is an enlarged diagram showing a grip, the first operating body, the second operating body, the guide pipe, the sheath, and the endoscope at a position indicated by a sign 10B in FIG. 8B.
Figure 11A:
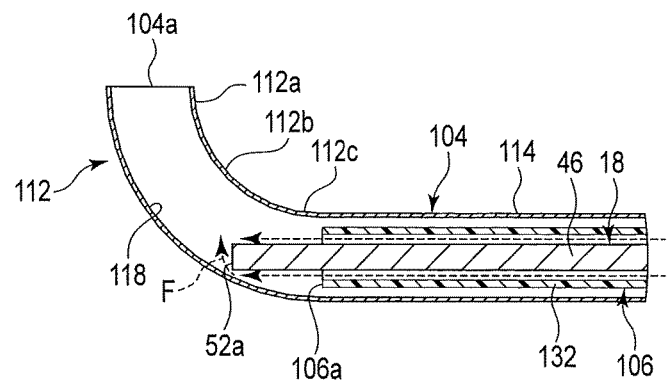
FIG. 11A is an enlarged diagram showing the guide pipe, the sheath, and the vicinity of the distal end of the insertion portion of the endoscope at a position indicated by a sign 11A in FIG. 9B.
Figure 11B:
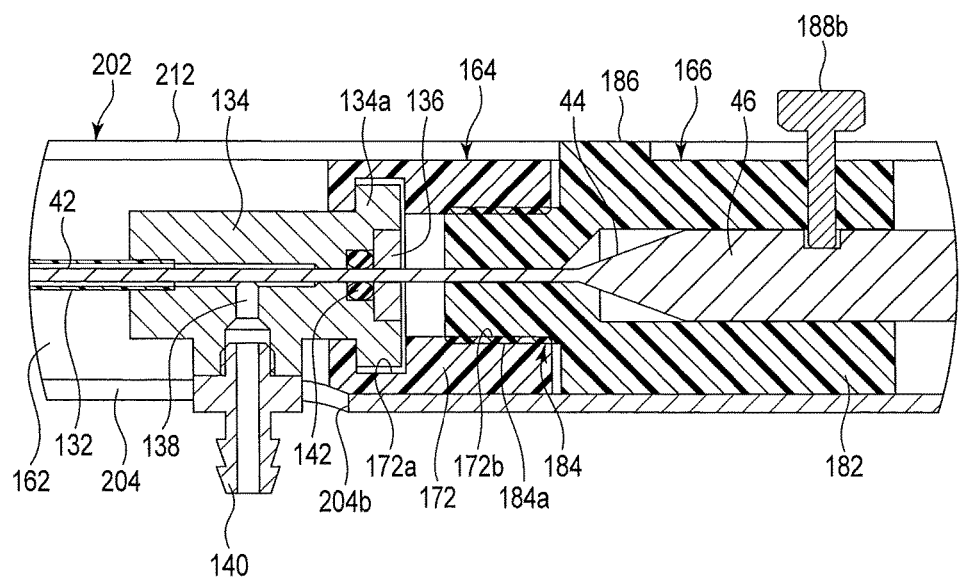
FIG. 11B is an enlarged diagram showing the grip, the first operating body, the second operating body, the guide pipe, the sheath, and the endoscope at a position indicated by a sign 11B in FIG. 9B.

As shown in FIG. 7, a diametrically outwardly protruding shaft (switch portion) 174a is formed in the outer circumferential surface of the cylindrical body 172 of the first operating body 164. A protrusion (switch portion) 174b is formed at the distal end of the shaft 174a located apart from the outer circumferential surface of the cylindrical body 172.

As shown in FIG. 3, the outer circumferential surface of the first cylindrical body 182 of the second operating body 166 is movable along the inner circumferential surface of the grip 162 of the handle unit 102.

As shown in FIG. 7, a diametrically outwardly protruding protrusion 186 is formed in the outer circumferential surface of the first cylindrical body 182 of the second operating body 166.

The inner circumferential surface of the second operating body 166 differs between the inside diameter on the distal side and the inside diameter on the proximal side. For example, the inside diameter of the second cylindrical body 184 is formed to be slightly larger than the outside diameter of the insertion portion 42 of the endoscope 18 and to be smaller than the maximum diameters of the anti-break 44 and the support portion 46. The inside diameter of the first cylindrical body 182 is formed to be slightly larger than the maximum outside diameter of the support portion 46 of the endoscope 18. The inner circumferential surface of the second operating body 166 can be formed suitably to the shapes of the proximal end of the insertion portion 42 of the endoscope 18 and the support portion 46. Thus, the insertion portion 42 and the support portion 46 of the endoscope 18 can be fitted in the inner circumferential surface of the second operating body 166.

As shown in FIG. 3 and FIG. 6A to FIG. 7, a through-hole 188 that intersects at right angles with the longitudinal axis L is formed in the first cylindrical body 182 of the second operating body 166 closer to the proximal side than the protrusion 186. An internal thread 188a is formed in the through-hole 188. The second operating body 166 has the external thread 188b screwed to the through-hole 188 and thus fixed to the recess 46a of the support portion 46 of the endoscope 18. Thus, the support portion 46 of the endoscope 18 moves to follow the movement of the second operating body 166 along the longitudinal axis L. Therefore, the second operating body 166 can move the insertion portion 42 of the endoscope 18 in its axial direction relative to the guide pipe 104.

As shown in FIG. 7, the outer circumferential surface of the second cylindrical body 184 of the second operating body 166 has an external-thread-shaped helical groove 184a closer to the distal side than the protrusion 186 of the first cylindrical body 182. The external-thread-shaped helical groove 184a of the second operating body 166 screws to the internal-thread-shaped helical groove 172b of the cylindrical body 172 of the first operating body 164. Thus, as shown in FIG. 3, the cylindrical body 172 of the first operating body 164 and the first cylindrical body 182 of the second operating body 166 can be brought closer and away along the longitudinal axis L.

As shown in FIG. 6A, the grip 162 of the handle unit 102 has a first guide passage 202 which guides the shaft 174a of the first operating body 164 and the protrusion 186 of the second operating body 166, and the second guide passage 204 which guides the tube connection portion 140 of the sheath 106. The first guide passage 202 and the second guide passage 204 allow communication between the inside and outside of the grip 162. The tube connection portion 140 is disposed across the inside and outside of the grip 162 through the second guide passage 204 of the grip 162.

The first guide passage 202 has a main line (first direction groove) 212 formed along the longitudinal axis L, and a sub-line (second direction groove) 214 which deviates from the main line 212. The main line 212 and the sub-line 214 are continuous. The main line 212 of the first guide passage 202 has a distal end 212a closer to the proximal side than the distal end 162a of the grip 162, and is formed continuously up to the proximal end 162b of the grip 162. The sub-line 214 of the first guide passage 202 extends along the circumferential direction that intersects at right angles with the longitudinal axis L in this embodiment. Thus, the main line 212 and the sub-line 214 of the first guide passage 202 are substantially T-shaped. The sub-line 214 of the first guide passage 202 does not need to extend along the circumferential direction that intersects at right angles with the longitudinal axis L. The sub-line 214 has only to extend in a direction that intersects with the longitudinal axis L.

As shown in FIG. 8A to FIG. 9B, the shaft 174a of the first operating body 164 is movable along the main line 212 and the sub-line 214 of the first guide passage 202. The protrusion 186 of the second operating body 166 is movable along the main line 212 of the first guide passage 202.

As shown in FIG. 6B, the second guide passage 204 is formed along the longitudinal axis L. That is, the second guide passage 204 is formed parallel to the main line 212 of the first guide passage 202. The second guide passage 204 has a distal end 204a closer to the proximal side than the distal end 162a of the grip 162, and a proximal end 204b closer to the distal side than the proximal end 162b of the grip 162. The second guide passage 204 is continuously formed between the distal end 204a and the proximal end 204b.

The treatment device 20 shown in FIG. 3 may be assembled in any manner, but is formed in the following manner by way of example.

The O-ring 142 is fixed to the sheath holder 134 with the fixing plate 136. The flange 134a of the sheath holder 134 is supported by the support portion 172a of the first operating body 164 in a state where the tube connection portion 140 is detached from the sheath holder 134. In this state, the flange 134a of the sheath holder 134 is supported by the first operating body 164. The second operating body 166 is screwed to the proximal side of the first operating body 164.

In this state, the first operating body 164 and the second operating body 166 are inserted into the grip 162 of the handle unit 102 from the proximal side of the grip 162. In this instance, the shaft 174a and the protrusion 174b of the first operating body 164 are moved along the main line 212 of the first guide passage 202, and the protrusion 186 of the second operating body 166 is moved along the main line 212 of the first guide passage 202. The distal opening 106a of the sheath 106 is then protruded from the distal end 162a of the grip 162 of the handle unit 102.

The tube connection portion 140 is connected to the sheath holder 134 through the second guide passage 204.

The holder 116 of the guide pipe 104 is fixed to the distal end 162a of the grip 162 of the handle unit 102.

In this instance, the first operating body 164 and the second operating body 166, that is, the movement mechanism 170 is used as a slider movable along the longitudinal axis L of the grip 162.

It is appropriate that a recess and a projection that give a click feel to the user be formed between the protrusion 174b of the first operating body 164 and/or the protrusion 186 of the second operating body 166 and the first guide passage 202 of the grip 162 when the shaft 174a and the protrusion 174b of the first operating body 164 are disposed at the intersection of the main line 212 and the sub-line 214.

The treatment device 20 shown in FIG. 3 is assembled as above. In this instance, as shown in FIG. 8A to FIG. 9B, a surface which is defined by the bending from the proximal end toward the distal end of the bent pipe 112 of the guide pipe 104 corresponds to a surface which passes through the longitudinal axis L and which extends along the line 8B-8B in FIG. 8A and a surface which passes through the longitudinal axis L and which extends along the line 9B-9B in FIG. 9A.

The distal end 42a of the insertion portion 42 of the endoscope 18 is then disposed in the sheath body 132 through the proximal end of the grip 162 of the handle unit 102, the second operating body 166, the first operating body 164, the fixing plate 136, the O-ring 142, and the sheath holder 134. As shown in FIG. 8A to FIG. 9B, the support portion 46 of the endoscope 18 is then disposed inside the second operating body 166, and the external thread 188b is fixed to the recess 46a of the support portion 46 of the endoscope 18 through the main line 212 of the first guide passage 202 of the grip 162 of the handle unit 102 and the through-hole 188 of the second operating body 166. In this way, the treatment device unit 12 is assembled. In this instance, in the treatment device unit 12, the insertion portion 42 of the endoscope 18, the sheath 106, and the guide pipe 104 are arranged in this order from the inside to the outside of the longitudinal axis L.

The support portion 46 of the endoscope 18 moves to follow the movement of the second operating body 166 along the longitudinal axis L. In the meantime, the support portion 46 of the endoscope 18 regulates the movement of the second operating body 166 around the longitudinal axis L by the edge of the main line 212 of the first guide passage 202.

The unintentional movement of the first operating body 164 and the second operating body 166 relative to the grip 162 of the handle unit 102 due to, for example, gravitation is regulated. This is attributed to, for example, friction between the outer circumferential surface of the sheath body 132 and the inner circumferential surface of the straight pipe 114 of the guide pipe 104, friction between the O-ring 142 and the outer circumferential surface of the insertion portion 42 of the endoscope 18, and the prevention of the movement of the second operating body 166 relative to the grip 162 of the handle unit 102 in a circumferential direction around the longitudinal axis.

It is preferable that a mark M indicating that the distal opening 106a of the sheath 106 and the distal surface 52a of the insertion portion 42 of the endoscope 18 correspond to the distal opening 104a of the guide pipe 104 be made in the outer circumference of the first guide passage 202 of the grip 162 based on the position of the protrusion 174b of the first operating body 164.

Next, functions of the treatment system 10 according to this embodiment, particularly, functions of the treatment device unit 12 are described. An example of the observation and treatment of paranasal sinuses using the treatment system 10 is described here. A series of treatments using the treatment system 10 is conducted as below.

(Step 0)

The treatment system 10 is prepared as below.

When the treatment system (endoscope system) 10 is used, the tube 26 is connected to the tube connection portion 140 of the treatment device unit 12. The controller 14 is also connected to the cable 48 of the endoscope 18.

As shown in FIG. 8A, FIG. 8B, FIG. 10A, and FIG. 10B, the distal surface 52a of the insertion portion 42 of the endoscope 18 corresponds or substantially corresponds to the distal opening 106a of the sheath 106 when the shaft 174a and the protrusion 174b of the first operating body 164 are located in the main line 212 of the first guide passage 202 (first state (movable state)). The user (surgeon) can then operate the protrusion 174b of the first operating body 164 and/or the protrusion 186 of the second operating body 166 along the main line 212. In this instance, it is possible to set the distal surface 52a of the insertion portion 42 of the endoscope 18 toward the bent surface 118 of the bent pipe 112 to display the bent surface 118 on the monitor 16, set the distal surface 52a of the insertion portion 42 of the endoscope 18 toward the distal opening 104a of the guide pipe 104 to display the distal opening 104a on the monitor 16, or protrude from the distal surface 52a of the insertion portion 42 of the endoscope 18 from the distal opening 104a to display the outside of the treatment device 20 on the monitor 16. When the shaft 174a and the protrusion 174b of the first operating body 164 are located at the intersection of the main line 212 and the sub-line 214 of the first guide passage 202, the distal opening 106a of the sheath 106 and the distal surface 52a of the insertion portion 42 of the endoscope 18 are disposed in the vicinity of the distal end of the straight pipe 114. In other words, the distal surface 52a of the insertion portion 42 of the endoscope 18 and the distal opening 106a of the sheath 106 are located in the vicinity of the proximal end of the bent pipe 112. This position is referred to as a neutral position.

At the neutral position, the bent surface (inner circumferential side region) 118 on the distal side of the curving portion 112c of the bent pipe 112 of the guide pipe 104 can be observed with the endoscope 18, but the distal end 112a cannot be observed. That is, the bent surface 118 on the distal side of the curving portion 112c of the bent pipe 112 of the guide pipe 104 is displayed on the monitor 16 at the neutral position.

When the shaft 174a and the protrusion 174b of the first operating body 164 are disposed at the intersection of the main line 212 and the sub-line 214 of the first guide passage 202 and disposed at the neutral position, a click feel is given to the user. Thus, the user can recognize that the shaft 174a and the protrusion 174b of the first operating body 164 are disposed at the neutral position without visually recognizing the grip 162.

As shown in FIG. 9A, FIG. 9B, FIG. 11A, and FIG. 11B, the distal opening 106a of the sheath 106 is kept disposed in the vicinity of the distal end of the straight pipe 114 when the shaft 174a and the protrusion 174b of the first operating body 164 are located in the sub-line 214 of the first guide passage 202 (second state (cleanable state)). The distal surface 52a of the insertion portion 42 of the endoscope 18 then protrudes relative to the distal opening 106a of the sheath 106. As the shaft 174a and the protrusion 174b of the first operating body 164 come closer to the distal end of the sub-line 214 from the main line 212, the protrusion amount of the distal surface 52a of the insertion portion 42 of the endoscope 18 relative to the distal opening 106a of the sheath 106 increases.

(Step 1)

The user (surgeon) grasps the handle unit 102. The user disposes the shaft 174a and the protrusion 174b of the first operating body 164 in the first state (movable state) and at the neutral position. In this state, the user moves the protrusion 174b of the first operating body 164 and/or the protrusion 186 of the second operating body 166 toward the distal side along the main line 212. The user then moves the shaft 174a and the protrusion 174b of the first operating body 164 so that the shaft 174a and the protrusion 174b will be adjacent to the mark M of the grip 162. In this instance, the positions of the distal surface 52a of the insertion portion 42 of the endoscope 18 and the distal opening 106a of the sheath 106 substantially correspond to the distal opening 104a of the guide pipe 104. In this instance, the outer circumferential surface of the distal surface 52a of the insertion portion 42 of the endoscope 18 is supported by the distal opening 106a of the sheath 106 and the distal opening 104a of the guide pipe 104. Thus, the direction in which the distal opening 104a of the guide pipe 104 is set is observed by the endoscope 18. This is referred to as a first observation state.

(Step 2)

The user guides the distal opening 104a of the guide pipe 104 of the treatment device unit 12, for example, to the entrance of a paranasal sinus from the external nostril while maintaining the first observation state. In this instance, the user inserts the distal opening 104a of the guide pipe 104 into the entrance (opening) of the paranasal sinus while displaying an observation image of the parts from the external nostril to the paranasal sinus on the monitor 16.

When the distal surface 52a of the insertion portion 42 of the endoscope 18 has come to a dead end in the image observed with the endoscope 18, an observation image showing the color of a mucous membrane is displayed on the entire monitor 16. On the other hand, when there is an insertion path ahead of the distal surface 52a of the insertion portion 42 of the endoscope 18, not only the mucous membrane but also a passage through a narrowed area is displayed on the monitor 16.

In this instance, the user suitably moves the grip 162 of the handle unit 102. The user then disposes the distal opening 104a of the guide pipe 104 at the entrance of the paranasal sinus.

(Step 3)

In a state where the distal opening 104a of the guide pipe 104 is disposed at the entrance of the paranasal sinus, the user moves the protrusion 174b of the first operating body 164 and/or the protrusion 186 of the second operating body 166 toward the distal side relative to the first observation state. The positions of the distal surface 52a of the insertion portion 42 of the endoscope 18 and the distal opening 106a of the sheath 106 are protruded relative to the distal opening 104a of the guide pipe 104. That is, the distal opening 106a of the sheath 106 and the distal end 42a of the insertion portion 42 are inserted into the paranasal sinus through the entrance of the paranasal sinus. This is referred to as a second observation state.

(Step 4)

In the second observation state, viscous matter may adhere to the distal surface 52a of the insertion portion 42 of the endoscope 18. In this case, the suction source 22 shown in FIG. 1 is activated to suck the viscous matter from the distal opening 106a of the sheath 106 through the space between the inner circumferential surface of the sheath 106 and the outer circumferential surface of the insertion portion 42 of the endoscope 18.

When the suction is difficult and the viscous matter keeps adhering to the distal end of the insertion portion 42 of the endoscope 18, the user activates the liquid supply source 24 to supply water through the space between the inner circumferential surface of the sheath 106 and the outer circumferential surface of the insertion portion 42 of the endoscope 18. In this instance, the physiological saline F is discharged from the space between the distal end of the inner circumferential surface of the sheath 106 and the outer circumferential surface of the distal end 42a of the insertion portion 42 of the endoscope 18. The suction source 22 is again activated in this state to suck the viscous matter and the physiological saline F from the distal opening 106a of the sheath 106 through the space between the inner circumferential surface of the sheath 106 and the outer circumferential surface of the insertion portion 42 of the endoscope 18.

(Step 5)

When the viscous matter still keeps adhering to the distal surface 52a of the insertion portion 42 of the endoscope 18 even after the action described in Step 4, the second observation state is replaced with the first observation state, and the neutral position is set while the distal opening 104a of the guide pipe 104 is kept disposed at the entrance of the paranasal sinus. In this instance, the user recognizes by a click feel that the protrusion 174b of the first operating body 164 is located at the intersection of the main line 212 and the sub-line 214 of the first guide passage 202 without visually recognizing the grip 162.

In this state, the user moves the protrusion 174b of the first operating body 164 toward a position which is most distal relative to the main line 212 in a range from the main line 212 to the sub-line 214. That is, the user disposes the shaft 174a and the protrusion 174b of the first operating body 164 in the second state (cleanable state). In this instance, the first operating body 164 rotates around the longitudinal axis L. The rotation of the second operating body 166 around the longitudinal axis L is regulated because the protrusion 186 and the external thread 188b are caught in the edge of the main line 212 of the first guide passage 202. Thus, if the first operating body 164 is rotated around the longitudinal axis L, the screwing state between the internal-thread-shaped helical groove 172b of the first operating body 164 and the external-thread-shaped helical groove 184a of the second operating body 166 changes. Specifically, the protrusion 186 of the second operating body 166 comes closer to the protrusion 174b of the first operating body 164. Thus, the distal surface 52a of the insertion portion 42 of the endoscope 18 protrudes relative to the distal opening 106a of the sheath 106. In this instance, the main line 212 and the sub-line 214 are formed to intersect at right angles with each other in this embodiment. Thus, the first operating body 164 cannot be moved relative to the main line 212. Therefore, the distal opening 106a of the sheath 106 is kept in the vicinity of the distal end of the straight pipe 114, that is, in the vicinity of the proximal end of the bent pipe 112.

Especially when the protrusion 174b of the first operating body 164 is moved to the position which is most distal to the main line 212 in the sub-line 214, the distal surface 52a of the insertion portion 42 of the endoscope 18 comes closest to or into abutment with the bent surface 118 in the inner circumferential surface of the bent pipe 112 of the guide pipe 104.

In this state, the user activates the liquid supply source 24 so that the physiological saline F flows through the space between the outer circumferential surface of the insertion portion 42 of the endoscope 18 and the inner circumferential surface of the sheath 106. The fixing plate 136 prevents the O-ring 142 from coming off the proximal side of the sheath holder 134 of the sheath 106. Thus, the O-ring 142 shown in FIG. 11B prevents the liquid which is supplied into the sheath holder 134 of the sheath 106 through the tube 26, the tube connection portion 140, and the T-shaped pipeline 138 from leaking out to the proximal side along the insertion portion 42 of the endoscope 18. Therefore, the physiological saline F can be guided toward the distal opening 106a of the body 132 of the sheath 106 when a gas or a liquid is supplied from the tube connection portion 140. The physiological saline F is then discharged from the distal opening 106a of the sheath 106 through the space between the inner circumferential surface of the sheath 106 and the outer circumferential surface of the insertion portion 42 of the endoscope 18. In this instance, the physiological saline F runs into the bent surface 118 in the inner circumferential surface of the bent pipe 112 of the guide pipe 104 and its direction is thus changed, and partly runs to the longitudinal axis L.

In this instance, tissue and other matter adhering to the distal surface 52a of the insertion portion 42 of the endoscope 18 is, for example, carried away by the liquid. Thus, the distal surface 52a of the insertion portion 42 of the endoscope 18 is cleaned by part of the physiological saline F. When the same flow volume of the physiological saline F is discharged at the same velocity, the matter adhering to the distal surface 52a of the insertion portion 42 of the endoscope 18 is more easily removed if the angle θ (see FIG. 4B) is larger. Thus, the flow volume per unit time to supply from the liquid supply source 24 may be adjusted in accordance with the angle θ when the distal surface 52a of the insertion portion 42 of the endoscope 18 is cleaned.

The display on the monitor 16 has only to be checked to find whether the viscous matter adhering to the distal surface 52a of the insertion portion 42 of the endoscope 18 has been removed.

When the viscous matter has been removed but the liquid adhering to the distal surface 52a of the insertion portion 42 of the endoscope 18 is displayed on the monitor 16, the user may remove the liquid from the tube connection portion 140 through the distal opening 106a of the sheath 106 by air blow in the same manner as the physiological saline F if the treatment system 10 has an air blow function. When the treatment system 10 has no air blow function, the user disposes the protrusion 174b of the first operating body 164 at the neutral position. That is, the first operating body 164 is rotated, and the protrusion 174b is moved from the state in which the protrusion 174b is disposed in the sub-line 214 to the state in which the protrusion 174b is disposed in the main line 212. That is, the distal surface 52a of the insertion portion 42 of the endoscope 18 is retracted relative to the distal opening 106a of the sheath 106 so that the position of the distal opening 106a of the sheath 106 corresponds or substantially corresponds to the position of the distal surface 52a of the insertion portion 42 of the endoscope 18. The user then activates the suction source 22 to remove the liquid adhering to the distal surface 52a of the insertion portion 42 of the endoscope 18 by suction. In this instance, the liquid discharged into the paranasal sinus can also be removed by suction.

(Step 6)

When again observing the inside of the paranasal sinus, the user operates the first operating body 164 and/or the second operating body 166 to set to the second observation state from the neutral position through the first observation state. The user then observes the monitor 16 with the endoscope 18 to check the state inside the paranasal sinus, for example, whether viscous matter has been accumulated, the state of the surface of the mucous membrane, the color and state of the mucus, and the state of the mucous membrane. That is, the user uses the observation image from the endoscope 18 to diagnose the inside of the paranasal sinus.

(Step 7)

The user cleans the inside of the paranasal sinus if necessary.

The fluid F, for example, the physiological saline is discharged into the paranasal sinus from the liquid supply source 24. After the inside of the paranasal sinus is cleaned with the physiological saline (cleaning solution) F, the physiological saline F including the viscous matter is sucked by the suction source 22. The second operating body 166 is then suitably rotated, and the first operating body 164 is rotated as required to check the color and volume of the mucous membrane inside the paranasal sinus on the monitor 16.

(Step 8)

The user treats the inside of the paranasal sinus if necessary. For example, the user administers medicine to the affected part inside the paranasal sinus.

The chemical is attached to the affected part from the liquid supply source 24 through the space between the inner circumferential surface of the sheath 106 and the outer circumferential surface of the insertion portion 42 of the endoscope 18.

(Step 9)

The user operates the first operating body 164 and/or the second operating body 166 to set to the first observation state from the second observation state. Alternatively, the user operates the first operating body 164 and/or the second operating body 166 to set to the neutral position from the second observation state. In this state, the user pulls the treatment device unit 12 of the treatment system 10 out of the paranasal sinus. In this instance, the distal opening 104a of the bent pipe 112 of the guide pipe 104 disposed at the entrance of the paranasal sinus is brought away from the entrance of the paranasal sinus so that abutment with mucosal tissues inside the nose is minimized, and the guide pipe 104 is pulled out of the nose.

As described above, the following can be said according to the treatment system 10 in this embodiment.

Owing to the movement mechanism 170 provided in the grip 162, the distal surface 52a of the insertion portion 42 of the endoscope 18 can be protruded more than the distal opening 106a of the sheath 106 and then brought closer to or into abutment with the bent surface 118 in the inner circumferential surface of the bent pipe 112 in a state where the distal opening 106a of the sheath 106 is disposed in the vicinity of the distal end of the straight pipe (second pipe) 114. Owing to the bent surface 118, the flow direction of the fluid F which is discharged from the distal opening 106a of the sheath 106 can be changed in a state where the distal opening 106a of the sheath 106 is disposed in the vicinity of the distal end of the straight pipe 114. The flow direction of the fluid F in particular can be changed from the direction toward the distal side from the distal opening 106a of the sheath 106 along the axial direction (longitudinal axis L) of the sheath 106 to the direction toward the distal surface 52a of the insertion portion 42 of the endoscope 18 which is close to or in abutment with the bent surface 118. It is therefore possible to apply the fluid F to the distal surface 52a and remove the matter adhering to the illumination window 56 and/or the light-receiving fibers 62.

Consequently, even if some matter adheres to the distal surface 52a of the insertion portion 42 of the endoscope 18 and the field of view is blocked, the matter adhering to the distal surface 52a of the insertion portion 42 of the endoscope 18 can be removed while the distal opening 104a of the guide pipe 104 is kept disposed at the entrance of the paranasal sinus.

When the protrusion 174b of the first operating body 164 is disposed at the intersection of the main line 212 and the sub-line 214 of the grip 162, the intersection of the main line 212 and the sub-line 214 can be used as a mark indicating that the distal opening 106a of the sheath 106 and the distal surface 52a of the insertion portion 42 of the endoscope 18 are disposed in the vicinity of the distal end of the straight pipe 114. Therefore, the user can easily find the neutral position.

For example, when the protrusion 174*b* of the first operating body 164 is located at the intersection of the main line 212 and the sub-line 214 of the first guide passage 202, the intersection permits the user to recognize that the distal opening 106*a* of the sheath 106 and the distal surface 52*a* of the insertion portion 42 of the endoscope 18 are retracted relative to the distal opening 104*a* of the guide pipe 104 even if the field of view of the endoscope 18 is not secured. It is appropriate that visual recognition not be possible but at least recognition be possible with a click feel when the protrusion 174*b* of the first operating body 164 is disposed at the intersection from the outside of the intersection.

In this embodiment, the mark M indicating that the distal end of the sheath 106 and the distal surface 52*a* of the insertion portion 42 of the endoscope 18 correspond to the distal opening 104*a* of the guide pipe 104 by the position of the protrusion 174*b* of the first operating body 164 is made at the position adjacent to the first guide passage 202 of the grip 162. Therefore, the user can easily recognize the position where the distal opening 106*a* of the sheath 106 is located relative to the distal opening 104*a* of the guide pipe 104 when the user moves the first operating body 164 relative to the grip 162 of the handle unit 102.

The user can bring the distal surface 52*a* of the insertion portion 42 of the endoscope 18 into a cleanable state inside the guide pipe 104 only by disposing the protrusion 174*b* of the first operating body 164 in the sub-line 214 from the neutral position that permits easy grasping. The user can perform this operation with the hand (one hand) holding the grip 162 while holding the grip 162 with the hand. Thus, operability of the treatment device 20 and the treatment system 10 can be improved.

In this embodiment, the tube connection portion (pipe sleeve) 140 can only be moved in a predetermined range between the distal end 204*a* and proximal end 204*b* of the second guide passage 204 of the grip 162. It is thus possible to prevent the movement mechanism 170 from being unintentionally pulled out of the grip 162.

The movement mechanism 170 according to this embodiment can move the second operating body 166 together with the movement of the first operating body 164 along the main line 212. Thus, the sheath 106 and the endoscope 18 can be moved together, so that the treatment device 20 according to this embodiment can improve operability for the user when the paranasal sinus is suitably observed and treated.

The shape of the bent pipe 112 of the guide pipe 104 according to this embodiment can be changed in accordance with a treatment target. Although not shown, the angle θ of the bent pipe 112 to the straight pipe 114 of the guide pipe 104 may be more than 90°. Thus, the guide pipe 104 in which the angle θ is more than 90° is preferably used to treat, for example, the maxillary sinus among paranasal sinuses.

Next, the second embodiment is described with reference to FIG. 12 to FIG. 19B. This embodiment is a modification of the first embodiment, and the same components or the components having the same functions as those described in the first embodiment are indicated by the same symbols as much as possible, and detailed explanations are not given.

Figure 12:
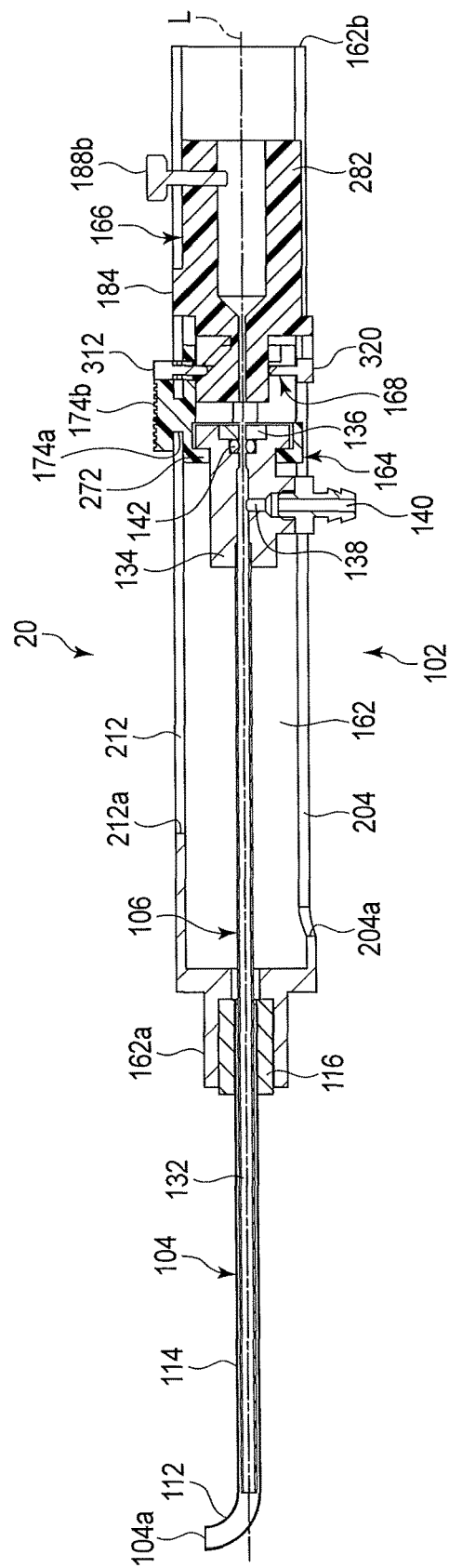
FIG. 12 is a schematic sectional view showing the treatment device, in the treatment system according to the second embodiment.

As shown in FIG. 12 to FIG. 13B, the handle unit 102 includes the grip 162, the first operating body 164 which supports and moves the sheath 106, the second operating body 166 which supports and moves the insertion portion 42 of the endoscope 18, and a switch button (switch portion) 168 provided between the first operating body 164 and the second operating body 166. The first operating body 164, the second operating body 166, and the switch button 168 constitute the movement mechanism 170. The grip 162, the first operating body 164, and the second operating body 166 of the handle unit 102 here are different in shape from the grip 162, the first operating body 164, and the second operating body 166 of the handle unit 102 described in the first embodiment.

As shown in FIG. 13A, the first guide passage 202 of the grip 162 has the main line (first direction groove) 212, and a through-groove (second direction groove) 216 which intersects at right angles with the main line 212 and which extends from the main line 212 in the circumferential direction. In contrast to the sub-line 214 described in the first embodiment extending from the main line 212 in one direction along the circumferential direction, the through-groove 216 extends from the main line 212 in two directions along the circumferential direction. Thus, the main line 212 and the through-groove 216 of the first guide passage 202 are formed substantially crosswise. A later-described first press body 312 of the switch button 168 can be put in and out of the through-groove 216.

The proximal end 204*b* of the second guide passage 204 of the grip 162 is located at the proximal end 162*b* of the grip 162 in this embodiment.

As shown in FIG. 14A to FIG. 15B, the first operating body 164 has a cylindrical body 272. The shaft 174*a* and the protrusion 174*b* are formed in the outer circumferential surface of the cylindrical body 272 of the first operating body 164 as has been described in the first embodiment. The shaft 174*a* and the protrusion 174*b* are movable along the main line 212 of the first guide passage 202.

The cylindrical body 272 of the first operating body 164 has the support portion 172*a* which supports the flange 134*a* of the sheath holder 134. The sheath holder 134 moves to follow the movement of the first operating body 164 along the longitudinal axis L.

A through-hole 274 having substantially the same shape as the through-groove 216 of the first guide passage 202 of the grip 162 of the handle unit 102 is formed in the cylindrical body 272 of the first operating body 164. The switch button 168 can be put into and taken out of the through-hole 274. That is, the switch button 168 is engaged with the first operating body 164. The later-described first press body 312 of the switch button 168 in particular can be put into and taken out of the through-hole 274.

A cutout 276 is formed at the position to face the through-hole 274 on the proximal side of the cylindrical body 272 of the first operating body 164. A pair of extensions 294*a* of a later-described second protrusion 294 of the second operating body 166 are provided in the cutout 276. Thus, interference in a case that the first operating body 164 and the second operating body 166 come close to or away from each other on the same axis, is prevented because the pair of extensions 294*a* of the second protrusion 294 of the second operating body 166 are provided in the cutout 276 of the first operating body 164.

The second operating body 166 has a cylindrical body 282 different from the one described in the first embodiment. The cylindrical bodies 272 and 282 have substantially the same outside diameter. The outside diameters of the cylindrical bodies 272 and 282 are formed to be slightly smaller than the inside diameter of the grip 162. Thus, as shown in FIG. 12, the outer circumferential surface of the cylindrical body 272 of the first operating body 164 and the outer circumferential surface of the first cylindrical body 182 of the second operating body 166 are movable along the inner circumferential surface of the grip 162 of the handle unit 102.

The protrusion 186 is formed in the outer circumferential surface of the cylindrical body 282 of the second operating body 166. The protrusion 186 is movable along the main line 212 of the first guide passage 202.

The through-hole 188 which intersects at right angles with the longitudinal axis L is formed in the cylindrical body 282 of the second operating body 166. The second operating body 166 has the external thread 188b screwed to the through-hole 188 and thus fixed to the recess 46a of the support portion 46 of the endoscope 18. Thus, the support portion 46 of the endoscope 18 moves to follow the movement of the second operating body 166 along the longitudinal axis L. Thus, the second operating body 166 can move the insertion portion 42 of the endoscope 18 relative to the guide pipe 104 in its axial direction.

The second operating body 166 has, on the distal side of the cylindrical body 282, an engagement portion 284 with which the later-described switch button 168 is engaged. Thus, the second operating body 166 cooperates with the first operating body 164 to engage the switch button 168. The engagement portion 284 has a first protrusion 292, the second protrusion 294, and a third protrusion 296 which each protrude to the distal side from the distal end of the cylindrical body 282 along the longitudinal axis L.

The first protrusion 292 is formed at a position including the central axis of the second operating body 166. Thus, the insertion portion 42 of the endoscope 18 is inserted through the first protrusion 292. The first protrusion 292 can come close to or away from the proximal surface of the first operating body 164 and has a distal surface 292a which intersects at right angles with the longitudinal axis L, a pair of side surfaces 292b which intersect at right angles with the distal surface 292a and which are parallel to the longitudinal axis L, a bottom surface 292c which intersects at right angles with the distal surface 292a and the side surfaces 292b, and an inclined surface 292d which is provided on the side opposite to the bottom surface 292c and which is inclined relative to the longitudinal axis L. The inclined surface 292d comes closer to the longitudinal axis L as the inclined surface 292d runs from the distal side to the proximal side along the longitudinal axis L.

The second protrusion 294 is disposed at a position close to the second guide passage 204 when the second operating body 166 is provided in the grip 162 of the handle unit 102. The second protrusion 294 has the pair of extensions 294a. The pair of extensions 294a extend along the longitudinal axis L, and face the bottom surface 292c of the first protrusion 292. The pair of extensions 294a are formed to be a predetermined distance. A second rod 318 and a second press body 320 are movable between the pair of extensions 294a.

The third protrusion 296 is disposed at a position close to the first guide passage 202 when the second operating body 166 is provided in the grip 162 of the handle unit 102. The third protrusion 296 has a pair of extensions 296a. The pair of extensions 296a extend along the longitudinal axis L. The pair of extensions 296a are formed to be a predetermined distance. A first rod 314 of the switch button 168 can be put into and taken out of the space between the pair of extensions 296a. The outer circumferential surfaces of the pair of extensions 296a are formed into a circular cylindrical shape. The pair of extensions 296a have inclined surfaces 296b facing the inclined surface 292d of the first protrusion 292.

The switch button 168 is provided between the first operating body 164 and the second operating body 166 to switch between the state (first state (movable state)) in which the first operating body 164 and the second operating body 166 are moved together when the protrusion 174b of the first operating body 164 or the protrusion 186 of the second operating body 166 is moved along the main line 212 of the first guide passage 202, and the state (second state (cleanable state)) in which the distal surface 52a of the insertion portion 42 of the endoscope 18 is cleaned inside the guide pipe 104. The switch button 168 is movable in two directions on a plane that intersects at right angles with the longitudinal axis L.

The switch button 168 includes the first press body 312 provided between the protrusion 174b of the first operating body 164 and the protrusion 186 of the second operating body 166, the first rod 314 which extends from the first press body 312 toward the longitudinal axis L, a rectangular body 316 coupled to the first rod 314, the second rod 318 which extends from the rectangular body 316 in a direction away from the longitudinal axis L, and the second press body 320 coupled to the second rod 318. It is preferable that the first press body 312, the first rod 314, the rectangular body 316, the second rod 318, and the second press body 320 are integrally formed in the switch button 168.

The rectangular body 316 has a first horizontal bar 322 which intersects at right angles with the first rod 314 and which is movable between the inclined surfaces 292d and 296b of the second operating body 166, a pair of vertical bars 324 which are respectively coupled to the ends of the first horizontal bar 322 and which are movable along the side surfaces 292b of the first protrusion 292 of the second operating body 166, and a second horizontal bar 326.

Figure 15A:
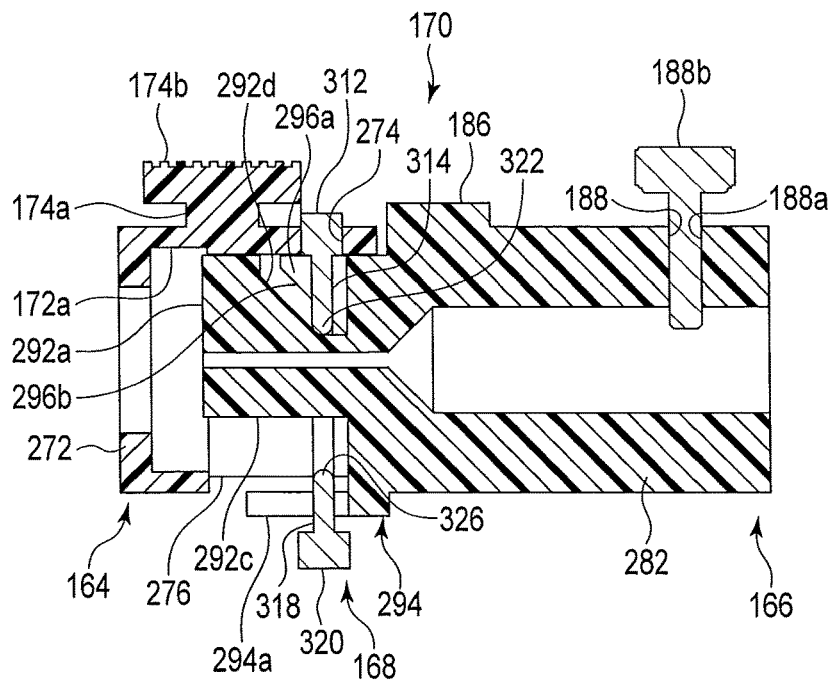
FIG. 15A is a schematic sectional view showing a state where a first press body of the press button of the handle unit of the treatment device is pressed toward the central axes of the first operating body and the second operating body to bring the distal surface of a first engagement portion of the second operating body closer to a support portion of the first operating body, in the treatment system according to the second embodiment.
Figure 15B:
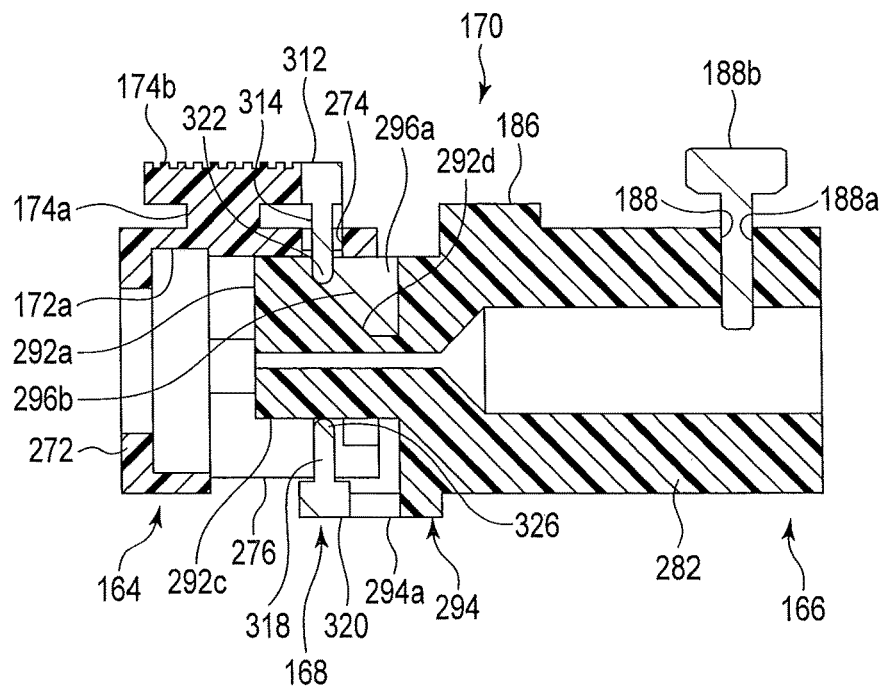
FIG. 15B is a schematic sectional view showing a state where a second press body of the press button of the handle unit of the treatment device is pressed toward the central axes of the first operating body and the second operating body to bring the distal surface of the first engagement portion of the second operating body away from the support portion of the first operating body, in the treatment system according to the second embodiment.
Figure 16A:
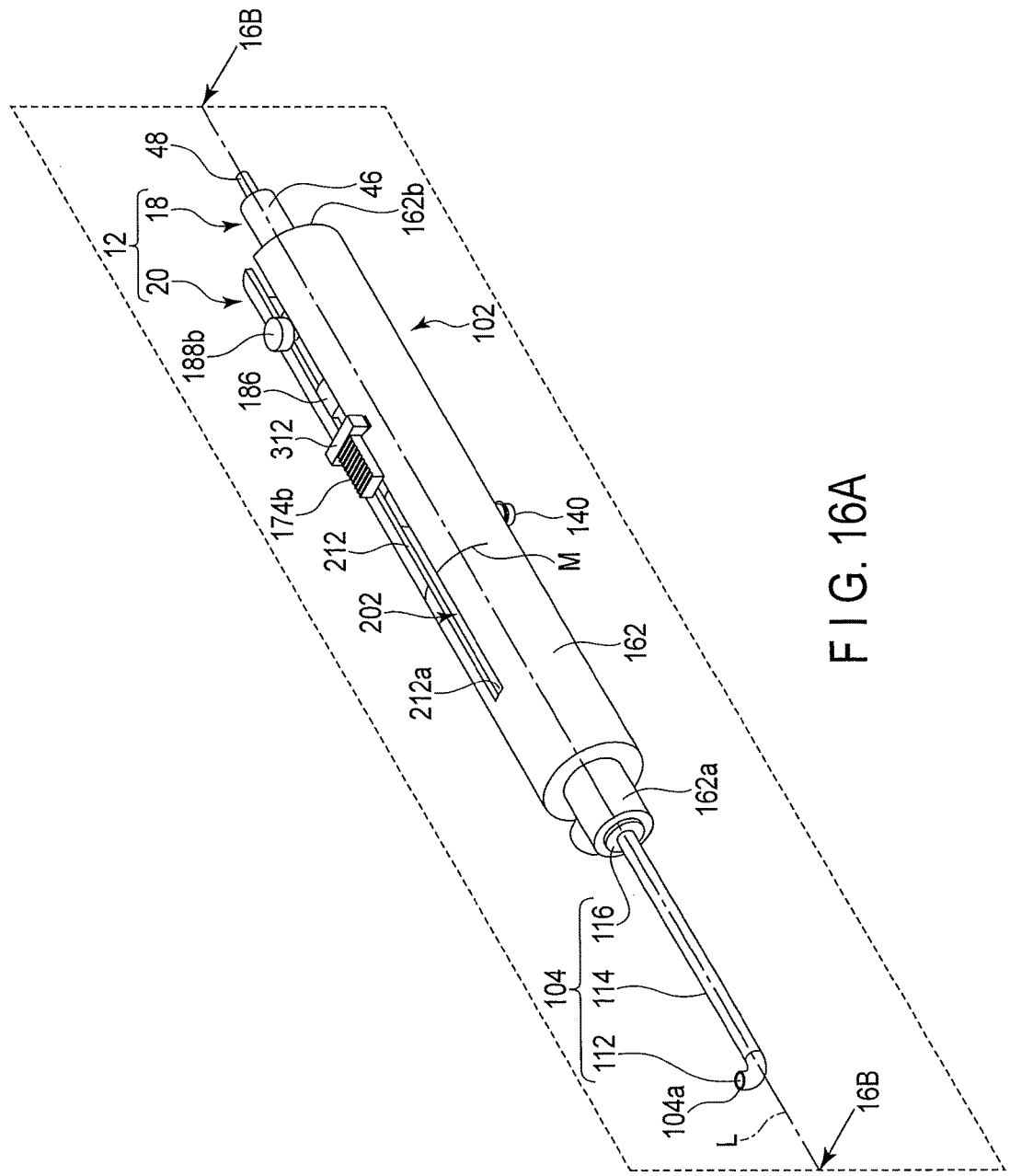
FIG. 16A is a schematic perspective view showing a state where the treatment device unit is seen from a direction similar to that in FIG. 13A, and showing a state where the inside of paranasal sinuses can be observed and treated with the treatment device unit, in the treatment system according to the second embodiment.
Figure 16B:
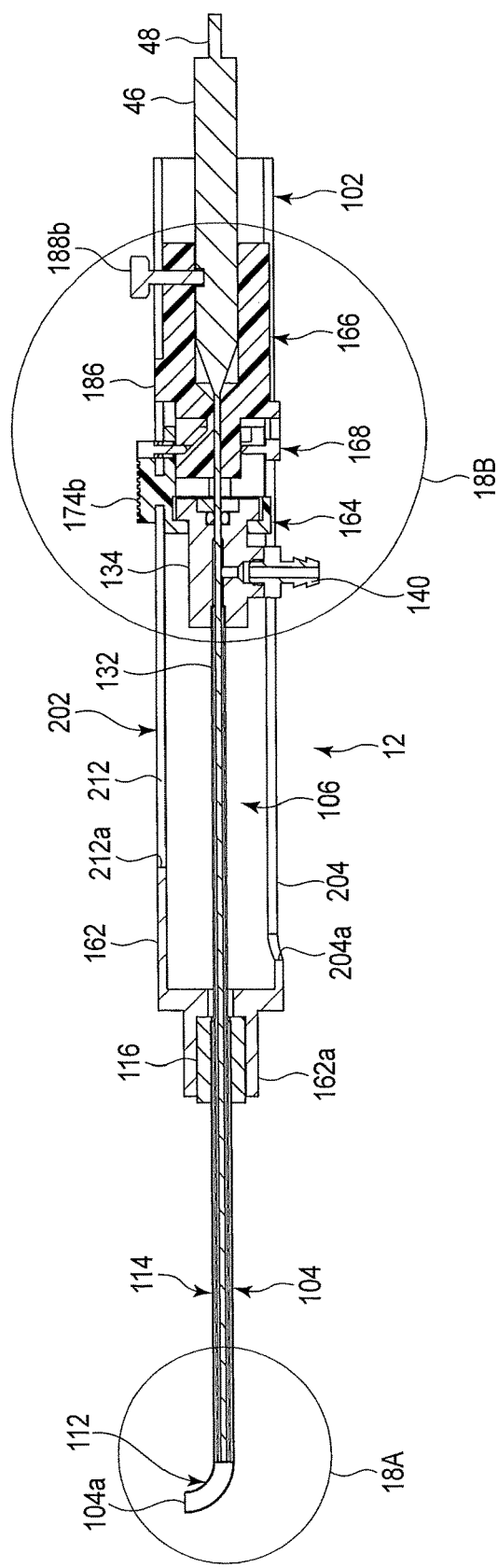
FIG. 16B is a longitudinal sectional view of the treatment device unit at a position along the line 16B-16B in FIG. 16A, in the treatment system according to the second embodiment.
Figure 17A:
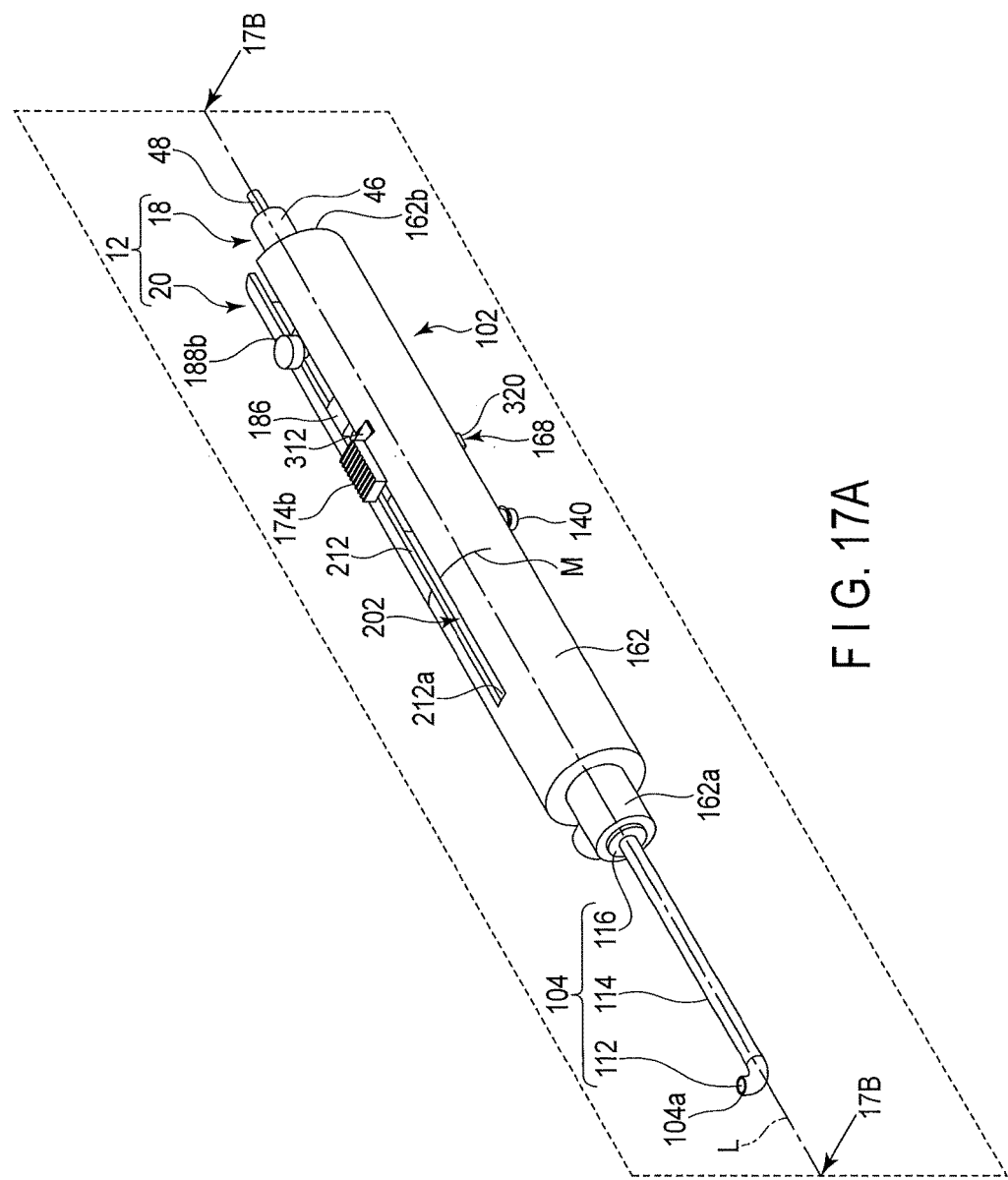
FIG. 17A is a schematic perspective view showing a state where the treatment device unit is seen from the direction similar to that in FIG. 13A, and showing a state where the distal surface of the insertion portion of the endoscope can be cleaned in the guide pipe of the treatment device unit, in the treatment system according to the second embodiment.
Figure 17B:
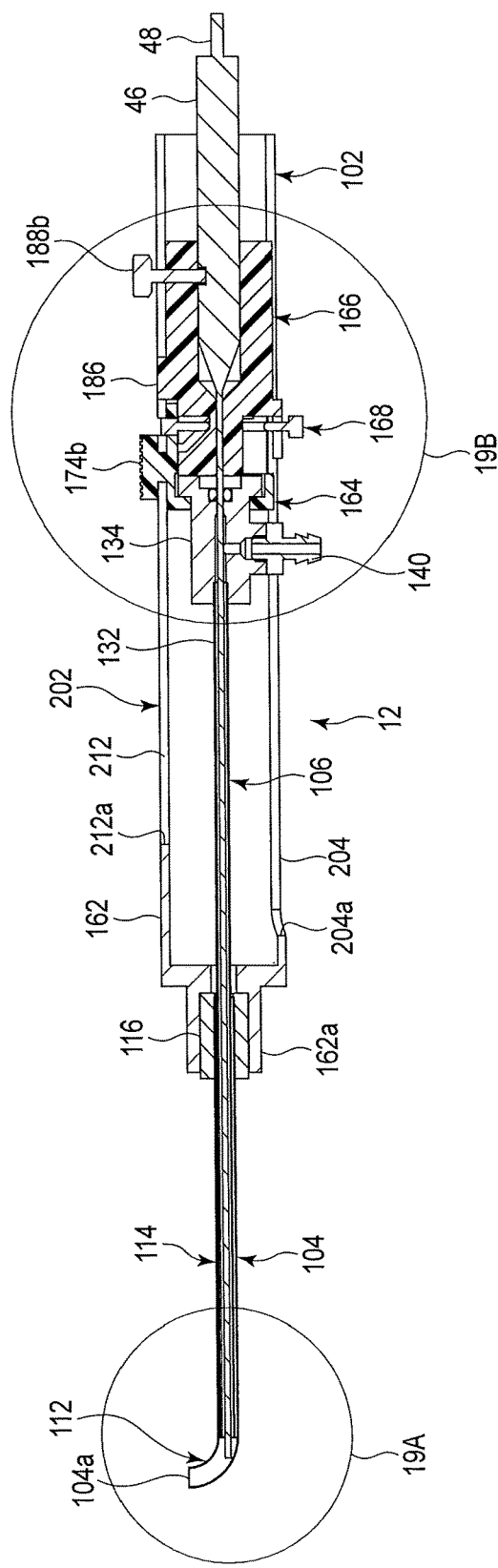
FIG. 17B is a longitudinal sectional view of the treatment device unit at a position along the line 17B-17B in FIG. 17A, in the treatment system according to the second embodiment.
Figure 18A:
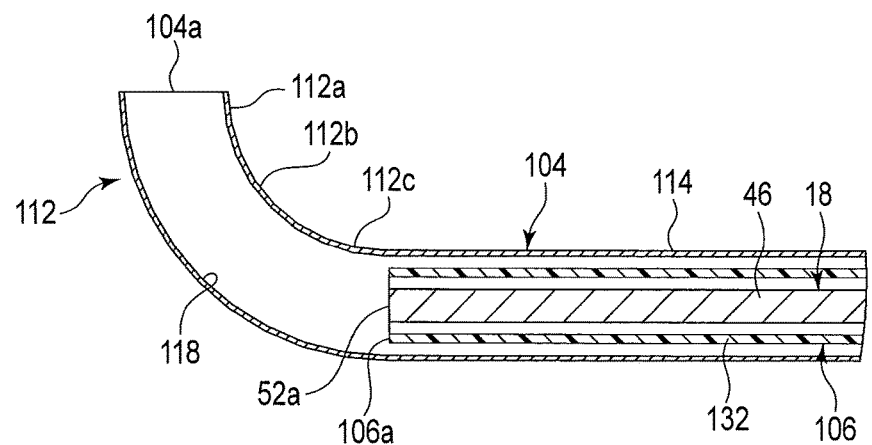
FIG. 18A is an enlarged diagram showing the guide pipe, the sheath, and the vicinity of the distal end of the insertion portion of the endoscope at a position indicated by a sign 18A in FIG. 16B.
Figure 18B:
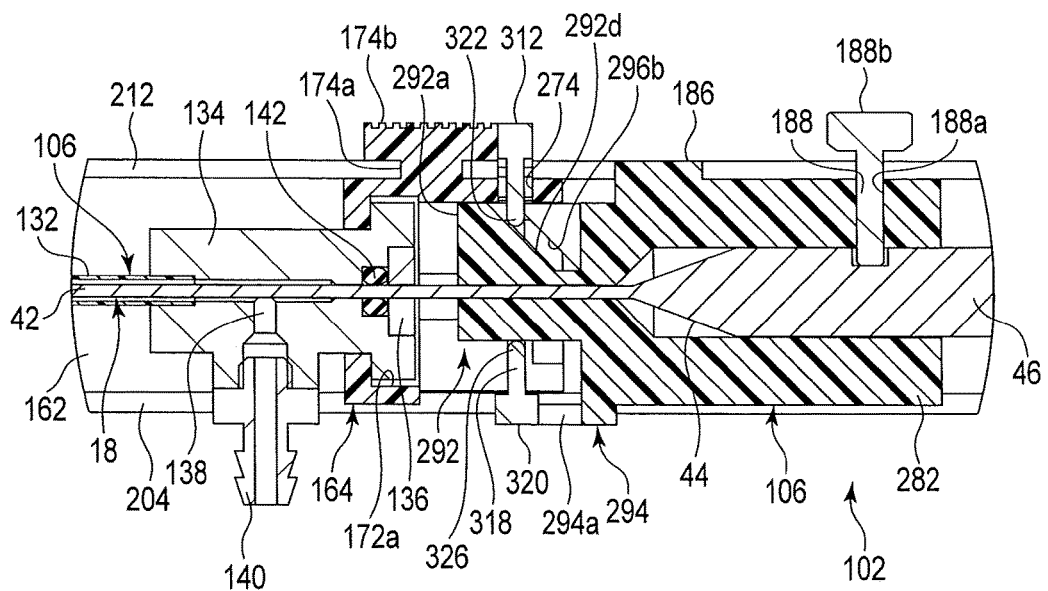
FIG. 18B is an enlarged diagram showing the grip, the first operating body, the second operating body, a switch button, the guide pipe, the sheath, and the endoscope at a position indicated by a sign 18B in FIG. 16B.

As shown in FIG. 15A and FIG. 15B, the first press body 312 of the switch button 168 is movable between a state to be disposed in the through-hole 274 of the first operating body 164 through the through-groove 216 of the grip 162 of the handle unit 102, and a state to protrude from the inside of the through-hole 274 and adjoin the proximal side of the protrusion 174b.

Figure 14A:
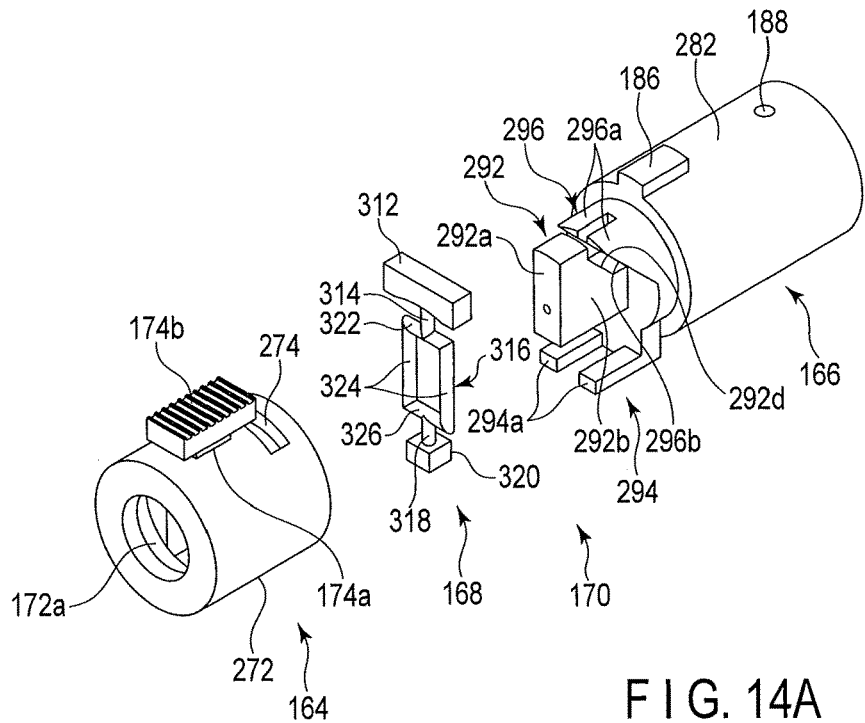
FIG. 14A is an exploded perspective view in which the first operating body, the second operating body, and a press button in FIG. 13A of the handle unit of the treatment device are shown in an enlarged form, in the treatment system according to the second embodiment.
Figure 14B:
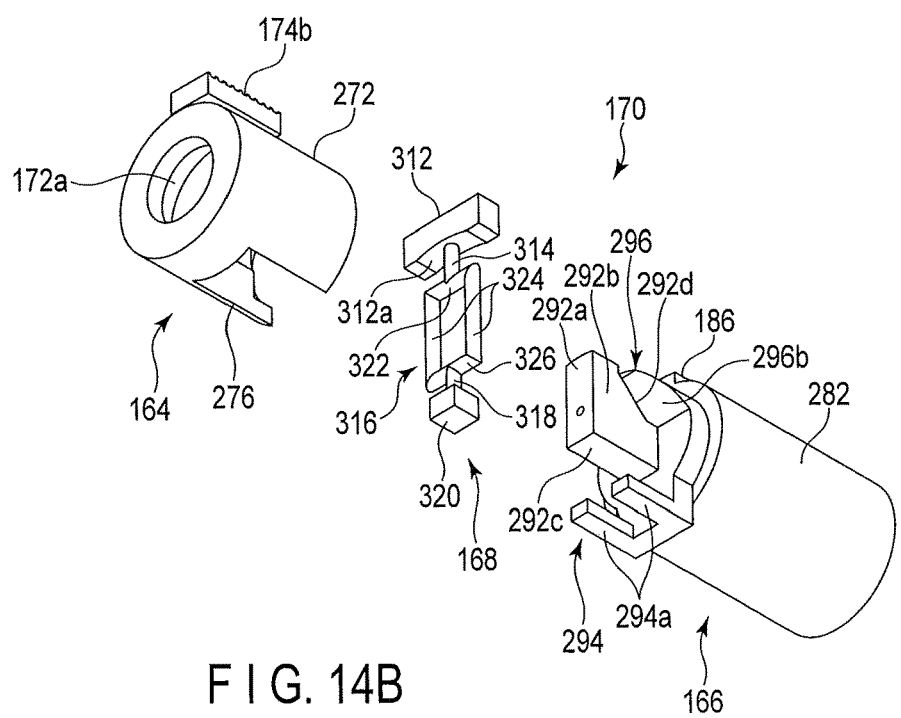
FIG. 14B is an exploded perspective view in which the first operating body, the second operating body, and the press button in FIG. 13B of the handle unit of the treatment device are shown in an enlarged form, in the treatment system according to the second embodiment.

As shown in FIG. 14B, the first press body 312 has a circular-arc portion 312a on the rear surface in which the first rod 314 extends. The radius of the circular-arc portion 312a is substantially the same as the radius of the outer circumferential surface of the third protrusion 296. Thus, the circular-arc portion 312a of the first press body 312 can be disposed on the outer circumferential surface of the third protrusion 296. In this instance, the protrusion amount of the first press body 312 to protrude in the outer circumferential surface of the grip 162 is suppressed.

The first rod 314 couples the first press body 312 to the first horizontal bar 322 of the rectangular body 316. The first rod 314 is coupled to the center of the width direction of the first horizontal bar 322 of the rectangular body 316 here.

The first horizontal bar 322 of the rectangular body 316 is disposed between the inclined surface 292d of the first protrusion 292 and the inclined surfaces 296b of the third protrusion 296. When the first press body 312 is disposed in the through-hole 274 and the first horizontal bar 322 is close to the longitudinal axis L, the distal surface 292a of the first protrusion 292 comes closer to the support portion 172a of the first operating body 164 along the longitudinal axis L. When the first press body 312 is taken out of the through-hole 274 and is adjacent to the proximal side of the protrusion 174b of the first operating body 164, the first horizontal bar 322 comes away from the longitudinal axis L, and the distal surface 292a of the first protrusion 292 comes away from the support portion 172a of the first operating body 164.

During such movement, the pair of vertical bars 324 of the rectangular body 316 move along the pair of side surfaces 292b of the first protrusion 292 in the direction that intersects with the longitudinal axis L. The second horizontal bar 326 of the rectangular body 316 comes close to or away from the bottom surface 292c of the first protrusion 292. The second horizontal bar 326 intersects at right angles with the extending direction of the pair of extensions 294a, and movably supports between the pair of extensions 294a and the bottom surface 292c of the first protrusion 292.

The second press body 320 can be disposed between the pair of extensions 294a.

In the movable state, the first press body 312, between the first press body 312 and the second press body 320 of the switch button 168, diametrically outwardly protrudes relative to the grip 162. In the cleanable state, the second press body 320, between the first press body 312 and the second press body 320 of the switch button 168, diametrically outwardly protrudes relative to the grip 162.

The structure is the same as that described in the first embodiment in other respects, and therefore no explanations are given.

Next, functions of the treatment system 10 according to this embodiment, particularly, functions of the treatment device unit 12 are described. A series of treatments using the treatment system 10 have been described in the first embodiment. Therefore, the example described here mainly regards the switch between the first state (movable state) in which the distal opening 106a of the sheath 106 and the distal surface 52a of the insertion portion 42 of the endoscope 18 are moved together relative to the distal opening 104a of the guide pipe 104, and the second state (cleanable state) in which the distal surface 52a of the insertion portion 42 of the endoscope 18 can be cleaned inside the guide pipe 104.

When the paranasal sinus is suitably observed and treated, the protrusion 174b of the first operating body 164 and the protrusion 186 of the second operating body 166 are disposed in the main line 212 of the first guide passage 202 relative to the grip 162 of the handle unit 102. Further, the first press body 312 of the switch button 168 is protruded relative to the outer circumferential surface of the grip 162 of the handle unit 102, and disposed at the position (first state (movable state)) adjacent to the proximal end of the first operating body 164. The second press body 320 of the switch button 168 is disposed between the pair of extensions 294a of the second protrusion 294 of the second operating body 166. In this instance, the distal surface 292a of the first protrusion 292 of the second operating body 166 is located away from the fixing plate 136 disposed in the first operating body 164. The distal surface 52a of the insertion portion 42 of the endoscope 18 and the distal opening 106a of the sheath 106 are located at substantially the same position along the longitudinal axis L.

The first press body 312 of the switch button 168 is disposed at the intersection of the main line 212 and the through-groove 216 of the first guide passage 202. This position is referred to as a neutral position. In this instance, the distal surface 52a of the insertion portion 42 of the endoscope 18 and the distal opening 106a of the sheath 106 are located in the vicinity of the distal end of the straight pipe 114 of the guide pipe 104. In other words, the distal surface 52a of the insertion portion 42 of the endoscope 18 and the distal opening 106a of the sheath 106 are located in the vicinity of the proximal end of the bent pipe 112 of the guide pipe 104.

In this state, the protrusion 174b of the first operating body 164 and/or the protrusion 186 of the second operating body 166 are/is moved along the main line 212 of the first guide passage 202. For example, the protrusion 174b of the first operating body 164 is moved toward the distal side along the longitudinal axis L. In this instance, a frictional action between the inner circumferential surface of the O-ring 142 disposed in the first operating body 164 and the outer circumferential surface of the insertion portion 42 of the endoscope 18 permits the distal surface 52a of the insertion portion 42 of the endoscope 18 and the distal opening 106a of the sheath 106 to correspond together to or protrude together relative to the distal opening 104a of the guide pipe 104.

For example, the protrusion 186 of the second operating body 166 is moved toward the distal side along the longitudinal axis L. In this instance, force is transmitted to the second operating body 166, the first press body 312 of the switch button 168, and the first operating body 164 in this order so that the distal surface 52a of the insertion portion 42 of the endoscope 18 and the distal opening 106a of the sheath 106 correspond together to or protrude together relative to the distal opening 104a of the guide pipe 104.

Thus, the user can set the first observation state that allows the observation of the direction in which the distal opening 104a of the guide pipe 104 faces, and can also set the second observation state in which the distal opening 106a of the sheath 106 and the distal end 42a of the insertion portion 42 are inserted in the paranasal sinus through the entrance of the paranasal sinus.

In the second observation state, the matter adhering to the distal surface 52a of the insertion portion 42 of the endoscope 18 can be removed, for example, by suction as has been described in the first embodiment.

In the switch button 168, the first press body 312 has a width greater than the width of the main line 212. Thus, the switch button 168 can be switched only when the switch button 168 is disposed in the through-groove 216 in this embodiment.

In the second observation state, when the viscous matter keeps adhering to the distal surface 52a of the insertion portion 42 of the endoscope 18, the second observation state is replaced with the first observation state, and the neutral position is set while the distal opening 104a of the guide pipe 104 is kept disposed at the entrance of the paranasal sinus. In this instance, the user recognizes by a click feel that the switch button 168 is located at the intersection of the main line 212 and the through-groove 216 of the first guide passage 202.

In this state, the user pushes in the first press body 312 of the switch button 168 toward the longitudinal axis L through the through-groove 216, and switches to the second state (cleanable state). In this instance, the first press body 312 of the switch button 168 remains adjacent to the proximal end of the protrusion 174b of the first operating body 164. The first horizontal bar 322 of the rectangular body 316 presses the inclined surface 292d of the first protrusion 292 of the second operating body 166. Thus, the second operating body 166 moves forward along the longitudinal axis L in a state where the first operating body 164 maintains its position relative to the grip 162 of the handle unit 102. In this instance, the distal surface 292a of the first protrusion 292 of the second operating body 166 comes close to or into abutment with the proximal surface of the first operating body 164, or comes close to or into abutment with the fixing plate 136. Thus, the distal surface 52a of the insertion portion 42 of the endoscope 18 fixed to the second operating body 166 moves forward relative to the distal opening 106a of the sheath 106 toward the distal side along the longitudinal axis L a distance equal to the movement distance of the second operating body 166. Since the first operating body 164 is not moved relative to the grip 162, the distal surface 52a of the insertion portion 42 of the endoscope 18 moves forward along the longitudinal axis L together with the forward movement of the second operating body 166 along the longitudinal axis L. The distal surface 52a of the insertion portion 42 of the endoscope 18 then comes into abutment with or close to the bent surface 118 in the inner circumferential surface of the bent pipe 112 of the guide pipe 104.

In this state, the user activates the liquid supply source 24 shown in FIG. 1 so that the physiological saline F, that is, the fluid F flows through the space between the outer circumferential surface of the insertion portion 42 of the endoscope 18 and the inner circumferential surface of the sheath 106. The user then discharges the physiological saline F from the distal end of the sheath 106. In this instance, the physiological saline F abuts on the inner circumferential surface of the sheath 106 and its direction is thus changed, and partly runs to the longitudinal axis L. In this instance, the distal surface 52a of the insertion portion 42 of the endoscope 18 is cleaned by part of the physiological saline F.

The display on the monitor 16 has only to be checked to find whether the viscous matter adhering to the distal surface 52a of the insertion portion 42 of the endoscope 18 has been removed.

When the viscous matter has been removed but the liquid is adhering to the distal surface 52a of the insertion portion 42 of the endoscope 18, the user may remove the liquid from the tube connection portion 140 through the distal opening 106a of the sheath 106 by air blow in the same manner as the physiological saline F if the treatment system 10 has an air blow function. When the treatment system 10 has no air blow function, the user disposes the protrusion 174b of the first operating body 164 at the neutral position. That is, the second press body 320 of the switch button 168 is pressed toward the longitudinal axis L, and the distal surface 52a of the insertion portion 42 of the endoscope 18 is retracted relative to the distal opening 106a of the sheath 106 so that the position of the distal opening 106a of the sheath 106 corresponds or substantially corresponds to the position of the distal surface 52a of the insertion portion 42 of the endoscope 18. The user then activates the suction source 22 to remove the liquid adhering to the distal surface 52a of the insertion portion 42 of the endoscope 18 by suction. In this instance, the liquid discharged into the paranasal sinus can also be removed by suction.

In this embodiment, the second operating body 166 can be moved to the proximal side relative to the first operating body 164 against the frictional force of the O-ring 142. Thus, it is possible to move the distal surface 52a of the insertion portion 42 of the endoscope 18 closer to the proximal side than the distal opening 106a of the sheath 106 by adjusting the amount of retraction of the distal surface 52a of the insertion portion 42 of the endoscope 18 relative to the sheath 106. In this case, the whole inner cavity of the sheath 106 can be used as a suction passage, an air supply passage, and a liquid supply passage.

As described above, the following can be said according to the treatment system 10 in this embodiment.

Owing to the movement mechanism 170 provided in the grip 162, the distal surface 52a of the insertion portion 42 of the endoscope 18 can be protruded more than the distal opening 106a of the sheath 106 and then brought closer to or into abutment with the bent surface 118 in the inner circumferential surface of the bent pipe 112 in a state where the distal opening 106a of the sheath 106 is disposed in the vicinity of the distal end of the straight pipe (second pipe) 114. Owing to the bent surface 118, the flow direction of the fluid F which is discharged from the distal opening 106a of the sheath 106 can be changed in a state where the distal opening 106a of the sheath 106 is disposed in the vicinity of the distal end of the straight pipe 114. The flow direction of the fluid F in particular can be changed from the direction toward the distal side from the distal opening 106a of the sheath 106 along the axial direction (longitudinal axis L) of the sheath 106 to the direction toward the distal surface 52a of the insertion portion 42 of the endoscope 18 which is close to or in abutment with the bent surface 118. It is therefore possible to apply the fluid F to the distal surface 52a and remove the matter adhering to the illumination window 56 and/or the light-receiving fibers 62.

The user can bring the distal surface 52a of the insertion portion 42 of the endoscope 18 into a cleanable state inside the guide pipe 104 merely by disposing the first press body 312 of the switch button 168 in the through-groove 216 of the grip 162 (see FIG. 15A) from the neutral position (see FIG. 15B) that permits easy grasping. The user can perform this operation with the hand (one hand) holding the grip 162 while holding the grip 162 with the hand. Thus, operability of the treatment device 20 and the treatment system 10 can be improved.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment device which is used together with an endoscope, the treatment device comprising:
    a sheath through which an insertion portion of the endoscope is inserted and which forms a passage for a fluid between the sheath and an outer circumferential surface of the insertion portion of the endoscope;
    a guide pipe provided outside the sheath,
    the guide pipe including:
        a first pipe which has:
            a curving portion, and
            an opening formed at a distal side of the curving portion and allowing a distal surface of the insertion portion of the endoscope and a distal end of the sheath to protrude from the opening of the guide pipe, and
        a second pipe which is continuous with a proximal side of the curving portion of the first pipe,
        the curving portion having, in its inner circumferential surface, a bent surface which is bent relative to the second pipe and which bends a flow direction of the fluid to be discharged from the distal end of the sheath in a state where the distal end of the sheath is located in a vicinity of a distal end of the second pipe;
    a grip disposed on a proximal side of the second pipe; and
    an operating body assembly which is provided in the grip and which is configured to protrude the distal surface of the insertion portion of the endo scope from the distal end of the sheath and is configured to bring the distal surface of the insertion portion of the endoscope closer to or into abutment with the bent surface according to an operation of the operating body assembly in a state where the distal end of the sheath is disposed in the vicinity of the distal end of the second pipe, wherein:

the operating body assembly includes a switch configured to switch between:
- a first state in which the sheath and the insertion portion of the endoscope are moved together; and
- a second state in which the insertion portion of the endoscope is moved relative to the sheath to protrude the distal surface of the insertion portion of the endoscope from the distal end of the sheath;

the grip includes a first direction groove, and a second direction groove which is continuous with the first direction groove and which extends in a direction that intersects with a longitudinal axis of the first direction groove;

the switch of the operating body assembly is configured to move the sheath and the endoscope together along the first direction groove in the first state, and the switch of the operating body assembly is movable through the second direction groove and is configured to protrude the distal surface of the insertion portion of the endoscope from the distal end of the sheath in the second state.

2. The treatment device according to claim 1, wherein the bent surface of the guide pipe bends the flow direction of the fluid from a direction toward a distal side of the sheath from the distal end of the sheath along an axial direction of the sheath to a direction toward the distal surface of the insertion portion of the endoscope which has been brought close to or into abutment with the bent surface in a state where the distal end of the sheath is disposed in the vicinity of the distal end of the second pipe, and the distal surface of the insertion portion of the endoscope is protruded from the distal end of the sheath.

3. The treatment device according to claim 1, wherein
an intersection of the first direction groove and the second direction groove is used as a mark, and
the distal end of the sheath is disposed in the vicinity of the distal end of the second pipe when the switch is located at the intersection of the first direction groove and the second direction groove.

4. The treatment device according to claim 1, wherein the distal surface of the insertion portion of the endoscope is configured to protrude from the distal end of the sheath and is close to or in abutment with the bent surface while the distal end of the sheath is kept disposed in the vicinity of the distal end of the second pipe when the switch is located in the second direction groove.

5. The treatment device according to claim 1, wherein
the operating body assembly, includes
a first operating body which holds a proximal end of the sheath and which has the switch, and
a second operating body which holds the endoscope and which is disposed concentrically with the first operating body and which is screwed to the first operating body, the first direction groove of the grip extends along a longitudinal axis of the grip, the second direction groove of the grip is continuous with the first direction groove of the grip and extends in a circumferential direction that deviates from the longitudinal axis of the grip, the sheath and the endoscope are moved together along the first direction groove when the switch is in the first state, and the second operating body is configured to rotate relative to the first operating body around the longitudinal axis of the grip to protrude the distal surface of the insertion portion of the endoscope from the distal end of the sheath when the switch is in the second state.

6. The treatment device according to claim 1, wherein
the operating body assembly includes
a first operating body which holds a proximal end of the sheath, and
a second operating body which holds the endoscope and which is disposed concentrically with the first operating body, and
the switch of the operating body assembly engages the first operating body and the second operating body switchably between the first state and the second state.

7. The treatment device according to claim 6, wherein
the switch is switched between the first state and the second state when the switch moves in a direction that intersects at right angles with the first direction groove and the second direction groove.

8. The treatment device according to claim 7, wherein the grip includes a guide passage having a proximal end and a distal end, the guide passage extending parallel to the first direction groove,
the sheath is provided with a pipe sleeve which allows the fluid to flow between the inner circumferential surface of the sheath and the outer circumferential surface of the insertion portion of the endoscope, and
the pipe sleeve is disposed across the inside and outside of the grip, and is movable between the distal end and proximal end of the guide passage.

9. The treatment device according to claim 1, wherein the sheath is provided with a pipe sleeve which allows the fluid to flow between the inner circumferential surface of the sheath and the outer circumferential surface of the insertion portion of the endoscope.

10. A treatment system comprising:
the treatment device according to claim 1; and
an endoscope having an optical element in its distal surface.

11. The treatment system according to claim 10, wherein the endoscope of a scan type is used.

* * * * *